US010391309B2

(12) United States Patent
Bloch et al.

(10) Patent No.: US 10,391,309 B2
(45) Date of Patent: Aug. 27, 2019

(54) SYSTEM FOR SELECTIVE SPATIOTEMPORAL STIMULATION OF THE SPINAL CORD

(71) Applicant: ECOLE POLYTECHNIQUE FEDERALE DE LAUSANNE (EPFL), Lausanne (CH)

(72) Inventors: Jocelyne Bloch, Paudex (CH); Grégoire Courtine, Lausanne (CH); Nikolaus Wenger, Berlin (DE); Silvestro Micera, St. Sulpice (CH); Marco Capogrosso, Pully (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 28 days.

(21) Appl. No.: 15/387,531

(22) Filed: Dec. 21, 2016

(65) Prior Publication Data

US 2017/0173326 A1 Jun. 22, 2017

(30) Foreign Application Priority Data

Dec. 22, 2015 (EP) .................................... 15201930

(51) Int. Cl.
*A61N 1/00* (2006.01)
*A61N 1/36* (2006.01)
(Continued)

(52) U.S. Cl.
CPC ........ *A61N 1/36003* (2013.01); *A61B 5/0488* (2013.01); *A61B 5/4836* (2013.01);
(Continued)

(58) Field of Classification Search
CPC ............ A61N 1/36003; A61N 18/0553; A61N 1/36067; A61N 1/36139; A61B 5/0488; A61B 5/4836
See application file for complete search history.

(56) References Cited

U.S. PATENT DOCUMENTS 5,643,330 A 7/1997 Holsheimer et al.
2006/0015153 A1* 1/2006 Gliner .................. A61N 1/3606 607/45
(Continued)

FOREIGN PATENT DOCUMENTS

EP 2868343 A1 5/2015
WO 2007047852 A2 4/2007
(Continued)

OTHER PUBLICATIONS

Rattay, F. et al., "Epidural electrical stimulation of posterior structures of the human lumbosacral cord: 2. quantitative analysis by computer modeling," Spinal Cord, vol. 38, No. 8, Aug. 2000, 17 pages.
(Continued)

*Primary Examiner* — Lindsey G Wehrheim
(74) *Attorney, Agent, or Firm* — McCoy Russell LLP

(57) ABSTRACT

The present disclosure refers to systems for electrical neurostimulation of a spinal cord of a subject in need of nervous system function support. In one example, a system comprises a signal processing device configured to receive signals from the subject and operate signal-processing algorithms to elaborate stimulation parameter settings; one or more multi-electrode arrays suitable to cover a portion of the spinal cord of the subject; and an Implantable Pulse Generator (IPG) configured to receive the stimulation parameter settings from the signal processing device and simultaneously deliver independent current or voltage pulses to the one or more multiple electrode arrays, wherein the independent current or voltage pulses provide multipolar spatiotemporal stimulation of spinal circuits and/or dorsal roots. Such system advantageously enables effective control of nervous system functions in the subject by stimulating the spinal
(Continued)

cord, such as the dorsal roots of the spinal cord, with spatiotemporal selectivity.

30 Claims, 11 Drawing Sheets

(51) Int. Cl.
*A61N 1/05* (2006.01)
*A61B 5/0488* (2006.01)
*A61B 5/00* (2006.01)

(52) U.S. Cl.
CPC ....... *A61N 1/0553* (2013.01); *A61N 1/36067* (2013.01); *A61N 1/36139* (2013.01)

(56) References Cited

U.S. PATENT DOCUMENTS

| | | | | |
|---|---|---|---|---|
| 2006/0122678 | A1 | 6/2006 | Olsen et al. | |
| 2007/0004567 | A1 | 1/2007 | Shetty et al. | |
| 2007/0168008 | A1 | 7/2007 | Olsen | |
| 2007/0179579 | A1 | 8/2007 | Feler et al. | |
| 2008/0294211 | A1 | 11/2008 | Moffitt | |
| 2010/0280570 | A1 | 11/2010 | Sturm et al. | |
| 2011/0093043 | A1* | 4/2011 | Torgerson ............ | A61N 1/0531 607/59 |
| 2014/0088674 | A1 | 3/2014 | Bradley | |

FOREIGN PATENT DOCUMENTS

| | | | |
|---|---|---|---|
| WO | 2013179230 | A1 | 12/2013 |
| WO | 2015000800 | A1 | 1/2015 |
| WO | 2015063127 | A1 | 5/2015 |

OTHER PUBLICATIONS

Herman, R. et al., "Spinal cord stimulation facilitates functional walking in a chronic, incomplete spinal cord injured," Spinal Cord, vol. 40, No. 2, Feb. 2002, 4 pages.

Yakavenko, S. et al., "Spatiotemporal Activation of Lumbosacral Motoneurons in the Locomotor Step Cycle," Journal of Neurophysiology, vol. 87, No. 3, Mar. 2002, 12 pages.

Ivanenko, Y. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, 11 page.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 2004, 11 pages.

Minassian, K. et al., "Stepping-like movements in humans with complete spinal cord injury induced by epidural stimulation of the lumbar cord: electromyographic study of compound muscle action potentials," Spinal Cord, vol. 42, No. 7, Jul. 2004, Published Online May 4, 2004, 16 pages.

Gerasimenko, Y. et al., "Spinal cord reflexes induced by epidural spinal cord stimulation in normal awake rats," Journal of Neuroscience Methods, vol. 157, No. 2, Oct. 30, 2006, Published Online Jun. 9, 2006, 11 pages.

Kiehn, O., "Locomotor Circuits in the Mammalian Spinal Cord," Annual Review of Neuroscience, vol. 29, Jul. 2006, 30 pages.

Barthelemy, D. et al., "Characteristics and Mechanisms of Locomotion Induced by Intraspinal Microstimulation and Dorsal Root Stimulation in Spinal Cats," Journal of Neurophysiology, vol. 97, No. 3, Mar. 2007, Published Online Jan. 10, 2007, 15 pages.

Edgerton, V. et al., "Training locomotor networks," Brain Research Reviews, vol. 57, Jan. 2008, Published Online Sep. 16, 2007, 14 pages.

Lavrov, I. et al., "Epidural Stimulation Induced Modulation of Spinal Locomotor Networks in Adult Spinal Rats," Journal of Neuroscience, vol. 28, No. 23, Jun. 4, 2008, 8 pages.

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.

Cappellini, G. et al., "Migration of Motor Pool Activity in the Spinal Cord Reflects Body Mechanics in Human Locomotion," Journal of Neurophysiology, vol. 104, No. 6, Dec. 2010, Published Online Sep. 29, 2010, 10 pages.

Ladenbauer, J. et al., "Stimulation of the Human Lumbar Spinal Cord With Implanted and Surface Electrodes: A Computer Simulation Study," IEEE Transactions n Neural Systems and Rehabilitation Engineering, vol. 18, No. 6, Dec. 2010, 9 pages.

Dominici, N. et al., "Locomotor Primitives in Newborn Babies and Their Development," Science Magazine, vol. 334, No. 6058, Nov. 18, 2011, 4 pages.

Dominci, N. et al., "Versatile robotic interface to evaluate, enable and train locomotion and balance after neuromotor disorders," Nature Medicine, vol. 18, No. 7, Jul. 2012, Published Online May 31, 2012, 8 pages.

Van Den Brand, R. et al., "Restoring Voluntary Control of Locomotion after Paralyzing Spinal Cord Injury," Science Magazine, vol. 336, No. 6085, Jun. 1, 2012, 5 pages.

Gad, P. et al., "Development of a multi-electrode array for spinal cord epidural stimulation to facilitate stepping and standing after a complete spinal cord injury in adult rats," Journal of Neuroengineering and Rehabilitation, vol. 10, No. 2, Jan. 21, 2013, 17 pages.

Lozano, A. et al., "Probing and Regulating Dysfunctional Circuits Using Deep Brain Stimulation," Neuron, vol. 77, No. 3, Feb. 6, 2013, 19 pages.

Holinski, B. et al., "Real-time control of walking using recordings from dorsal root ganglia," Journal of Neural Engineering, vol. 10, No. 5, Oct. 2013, Published Online Aug. 8, 2013, 15 pages.

Borton, D. et al., "Corticospinal neuroprostheses to restore locomotion after spinal cord injury," Neuroscience Research, vol. 78, No. 21-9, Jan. 2014, Published Online Oct. 14, 2013, 9 pages.

Borton, D. et al., "Personalized Neuroprosthetics," Science Translational Medicine, vol. 5, No. 210, Nov. 6, 2013, 13 pages.

Capogrosso, M. et al., "A Computational Model for Epidural Electrical Stimulation of Spinal Sensorimotor Circuits," Journal of Neuroscience, vol. 33, No. 49, Dec. 4, 2013, 15 pages.

Sayenko, D. et al., "Neuromodulation of evoked muscle potentials induced by epidural spinal-cord stimulation in paralyzed individuals," Journal of Neurophysiology, vol. 111, No. 5, Mar. 2014, Published Online Dec. 11, 2013, 12 pages.

Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.

Zhang, T. et al., "Mechanisms and models of spinal cord stimulation for the treatment of neuropathic pain," Brain Research, vol. 1569, Jun. 20, 2014, Published Online May 4, 2014, 13 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Minev, I. et al., "Electronic dura mater for long-term multimodal neural interfaces," Science Magazine, vol. 347, No. 6218, Jan. 9, 2015, 6 pages.

Danner, S. et al., "Human spinal locomotor control is based on flexibly organized burst generators," Brain: A Journal of Neurology, vol. 138, No. 3, Mar. 1, 2015, Published Online Jan. 12, 2015, 12 pages.

Hofstoetter, U. et al., "Periodic modulation of repetitively elicited monosynaptic reflexes of the human lumbosacral spinal cord," Journal of Neurophysiology, vol. 114, No. 1, Jul. 2015, Published Online Apr. 22, 2015, 11 pages.

Rejc, E. et al., "Effects of Lumbosacral Spinal Cord Epidural Stimulation for Standing after Chronic Complete Paralysis in Humans," PLoS One, vol. 10, No. 7, Jul. 24, 2015, 20 pages.

Gerasimenko, Y. et al., "Noninvasive Reactivation of Motor Descending Control after Paralysis," Journal of Neurotrauma, vol. 32, No. 24, Dec. 15, 2015, Published Online Aug. 20, 2015, 13 pages.

(56) References Cited

OTHER PUBLICATIONS

European Patent Office, Extended European Search Report Issued in Application No. 15201930.3, dated Mar. 9, 2016, Germany, 6 pages.
Guyatt, G. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al. "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground

(56) References Cited

OTHER PUBLICATIONS walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.

* cited by examiner

SYSTEM FOR SELECTIVE SPATIOTEMPORAL STIMULATION OF THE SPINAL CORD

CROSS-REFERENCE TO RELATED APPLICATIONS

The present application claims priority to European Patent Application No. 15201930.3, entitled "System for Selective Spatiotemporal Stimulation of the Spinal Cord," filed Dec. 22, 2015, the entire contents of which are hereby incorporated by reference for all purposes.

TECHNICAL FIELD

The present disclosure refers to the field of spinal cord neuro-prostheses for motor disorders.

In particular, it refers to systems for selective spatiotemporal stimulation of the spinal cord.

BACKGROUND OF THE PRESENT DISCLOSURE

Various neurological disorders disrupt the communication matrix between supraspinal centers and spinal circuits, which leads to a range of motor disabilities.

For example, a neuromotor impairment can be consequent to a spinal cord injury (SCI), an ischemic injury resulting from a stroke, or a neurodegenerative disease, such as Parkinson's disease.

In particular, after spinal cord lesion, either cervical or thoracic, motorpools do not receive inputs from the supraspinal structures despite spinal motor circuits remaining functional.

Neuromodulation strategies provide access to surviving circuits and pathways to alleviate these deficits (1, 2). In particular, electrical and chemical neuromodulation of the lumbar spinal cord has mediated significant improvement of lower-limb motor control in animal models (3-7) and humans (6, 8-11) with SCI.

Computer simulations (12-14) and experimental studies (7, 15-17) have provided evidence that electrical neuromodulation applied to the dorsal aspect of lumbar segments primarily engages proprioceptive feedback circuits recruited by the stimulation of dorsal roots fibers. The prevailing view is that the recruitment of these neural pathways activates central-pattern generating networks (9, 18) and raises the excitability of spinal circuits to a level that enables sensory information to become a source of motor control (19).

However, movement production is orchestrated by the coordinated activation of motorpools along the spinal cord that are activated with specific and precise timing by the central nervous system.

In particular, the production of limb movements involves the activation of spatially distributed motoneurons (21, 22) following precise temporal sequences (23, 24) that are continuously adjusted through sensory feedback (25).

Therefore, effective therapies should aim at the precise activation of spinal circuits in space and time.

This framework enacted two fundamental limitations in the clinical application of electrical neuromodulation therapies. First, the spatial location of stimulation remains confined to single spinal cord regions that are selected using empirical mapping experiments (9, 20). Second, the temporal structure of stimulation protocols is restricted to nonmodulated patterns that remain constant during motor execution, regardless of the current state of lower-limb movements (8, 9, 15).

Therefore, the design of spatiotemporal neuromodulation therapies to facilitate motor control in clinical settings relies on a series of non-trivial methodological developments. First, the design of spatially selective implants that can specifically target motor circuits via the recruitment of dorsal roots fibers. Second, the design of time specific stimulation patterns that target in real-time motoneurons located in spatially restricted regions.

Current stimulation protocols and systems do not attempt to reproduce these spatiotemporal patterns of motoneuron activation to facilitate movement. Indeed, they remain unspecific, restricted to single regions and delivered continuously.

Therefore, there is the need of a system integrating spatial selectivity and temporal structure to improve stimulation efficacy and thus motor control.

In particular, there is still the need of a system for stimulating specific spinal roots with a precise temporal resolution so that different, specific motor-pools can be activated during different gait phases.

Computational models and experimental works (12, 13, 15, 16) have shown that epidural electrical stimulation (EES) of the lumbar spinal cord mainly recruits large myelinated afferents fibers located in the dorsal roots. Efferent fibers can also be recruited in particular at the caudal/sacral level. After spinal cord injury, during non-specific EES, muscle activity is composed of a burst of monosynaptic and poly-synaptic components produced by the recruitment of dorsal root afferents often termed spinal reflexes (12). This muscle activity is modulated (7, 12) and gated by the spinal circuitry to build locomotor patterns and modulate kinematic variables (7).

These results have been obtained in experimental animals and humans with severe motor deficits (9, 19).

However, incomplete lesions can also result in the impossibility of movement despite remaining motor control abilities.

Moreover clinical lesions differ from case to case due to the variability in the nature, location and severity of the lesion. Each patient shows specific motor deficits that have to be selectively targeted to regain motor functions.

In order to selectively correct these deficits, the effects of EES should be focused on the impaired joint/functions. Joint/function specific EES would thus require the selective stimulation of a subset of dorsal roots in order to trigger joint/function specific spinal reflexes.

In view of the above, spinal dorsal roots should be selectively targeted in order to promote specific limb movements thus allowing restoration of motion.

Furthermore, in order to ensure a sufficient level of specificity, single rootlets should be targeted, granting in this way the access to motorpools located at specific segments thus improving muscle specificity.

The use of multi-electrode array devices for epidural stimulation in the rehabilitation of spinal cord injuries is known (33).

However, they are not able to achieve a high specificity of stimulation, in particular of specifically selected dorsal roots and muscles.

Indeed, state of the art multi-electrode arrays are designed to activate specific spinal segments based on the close proximity between the electrode and the said stimulated segment. Accordingly, the electrodes are placed on the dorsal surface of the cord, at regular intervals along the rostro-caudal extent based on the underlying longitudinal segmental structure. This design was mainly driven from pain applications, where the dorsal column fibers are targeted. Indeed, current clinical devices have been designed to specifically target myelinated fibers contained in dorsal columns to suppress neuropathic pain according to the gate theory (26).

In view of the above, there is still the need of a system for a selective spatial targeting and stimulation of specific spinal roots, in particular spinal dorsal roots.

As mentioned above, devices for spinal neurostimulation are known in the art of pain treatment.

US20070179579 discloses a method for neurostimulation to treat multiple pain locations. In the method, a multi-column, multi-row paddle lead is used to stimulate dorsal column fibers to act on pain locations. Electrode combinations are determined to address the pain and an implantable pulse generator (IPG) is used to deliver pulses according to said electrode combinations.

US2010280570 discloses an apparatus for stimulating the spinal cord for pain treatment, wherein the spinal cord contact surfaces are arranged in a plurality of rows, wherein the rows extend in a transverse direction to the extent of the spinal cord and adjacent rows of stimulation contact surfaces are arranged at a distance from one another in the direction of the extent of the spinal cord.

U.S. Pat. No. 5,643,330 discloses an apparatus for EES using a multi-channel pulse generator and an electrode transverse and facing the spinal cord.

US20070168008 and US2006122678 disclose a transverse tripole stimulation in which electrodes can be arranged in a direction transverse relative to the spinal cord.

US2007179579 discloses a paddle lead, which can be implanted in a patient for pain treatment.

US2014088674 discloses targeting spinal roots (dorsal and ventral) and motor nerve rootlets for pain treatment.

The above disclosed devices are used for pain treatment. This is a completely different field from the one of motor disorders, which is the field of the present disclosure. Indeed, in pain treatment, accidental movements are a side effect of the treatment and therefore should be carefully avoided. Devices are designed and used in order to target the spinal regions involved in pain and to avoid targeting of spinal regions involved in locomotion. On the contrary, the aim of the present application is the achievement of locomotion and in particular the specific target of the spinal structures involved in movement production.

It has now been found a system for electrical neuromodulation therapies capable of integrating spatial selectivity and temporal structure matching the natural dynamics of motoneuron activation and improve stimulation efficacy, enhancing the quality and vigor of lower-limb movements after SCI.

In particular, it has been found a stimulation system able to spatially and temporally specifically target the spinal dorsal roots in order to achieve a more selective activation of the desired motor circuits and therefore a more efficient movement production.

It has further been found that a multi-electrode array tailored to the dorsal roots anatomy together with multipolar stimulation allows modulating the shape of the stimulating field thus increasing stimulation specificity.

SUMMARY OF THE PRESENT DISCLOSURE

An object of the present disclosure is a system for spatiotemporal electrical neurostimulation of the spinal cord of a subject comprising:

a) a signal processing device receiving signals from said subject and operating signal-processing algorithms to elaborate stimulation parameter settings, operatively connected with b) an Implantable Pulse Generator (IPG) receiving stimulation parameter settings from said signal processing device a) and able to simultaneously deliver independent current or voltage pulses to one or more multiple electrode arrays; operatively connected with c) one or more multi-electrode arrays suitable to cover at least a portion of the spinal cord of said subject for applying to said subject a selective spatiotemporal stimulation of the spinal circuits and/or dorsal roots, wherein said IPG b) is operatively connected with said one or more multi-electrode arrays to provide a multipolar stimulation.

The above system according to the present disclosure advantageously allows achieving effective control of nervous functions, e.g., by selectively stimulating dorsal roots of a spinal cord in a subject needing control of nervous functions. Dorsal root multipolar stimulation is characterized by spatiotemporal selectivity. Nervous functions can be, but are not limited to, locomotor functions, muscle stimulation, or the like. Possible applications can be but are not limited to restoring or enhancing of locomotor functions, pain treatment, restoring or enhancing immunological functions and/or the immune system, awareness or consciousness, restoring or enhancing bowel function, restoring or enhancing sexual function, restoring or enhancing cardiovascular function, restoring or enhancing bladder function, restoring or enhancing gastrointestinal function, especially function of sphincters in the gastrointestinal tract like the sphincters of the stomach.

In said system, said signal processing device provides said IPG with stimulation parameter settings according to information from the subject provided by said signals, for example according to the specific gait phase or to gait parameters such as muscle activity, step height and foot acceleration.

In an example embodiment, said IPG receives said settings from said signal processing device with minimum delay.

An exemplary stimulation parameter setting comprises electrode combinations, e.g., information on which electrodes should be triggered, and current configuration.

Said signals from the subject can be neural signals, signals providing features of motion of said subject, kinematic signals and/or electromyography signals.

Said signals can be obtained, for example, by motion tracking systems, accelerometers, gyroscopes, force sensors, electromyographic sensors, neural sensors, and muscular sensors.

In an example embodiment, such signals detect the trajectory of each limb and provide the information to the signal processing device, which calculates the optimal stimulation parameter settings and triggers the activation of specific combinations of electrodes of the multi-electrode array via the IPG.

In an example embodiment, the On and Off states of electrodes targeting extensor- and flexor-related hotspots are triggered when the angular coordinates of limb endpoints cross user-defined thresholds.

The system of the present disclosure allows stimulating specific segments of the spinal cord of a subject with spatiotemporal selectivity thus improving limb movements when compared to continuous neuromodulation.

In an example embodiment, said IPG b) comprises a neutral returning electrode as reference.

In an example embodiment, said signal processing device a) is included in said IPG b).

Said multi-electrode array is placed epidurally or subdurally.

The use of a multi-electrode array specifically tailored to the anatomy of the dorsal roots allows for selective stimulation of the dorsal roots projecting to distinct spinal segments. Such selective stimulation allows the induction of specific muscular responses thus allowing the restoration of motion.

In an example embodiment said multi-electrode array comprises:

at least one portion comprising electrodes arranged in a direction transverse relative to the spinal cord and at least one portion comprising electrodes arranged in a longitudinal direction relative to the spinal cord.

Preferably, such transversal and longitudinal portions are alternately disposed in the array.

The transversal portion of the multi-electrode array according to the present disclosure engages the dorsal roots of the spinal cord in a "ring" configuration, thus surrounding the dorsal side of the spinal cord in such a way that it is possible to accurately select the dorsal root(s) to be stimulated. This can be achieved by operatively setting the signal processing device a) and IPG b) to adjust the multipolar stimulation in order to "focus" the desired target dorsal root. This will be explained in more detail by referring to FIG. 4.

Preferably, said array is used when stimulation of lumbar spinal roots is desired.

In another preferred embodiment, said multi-electrode array comprises multiple electrodes arranged in two or more columns disposed in a longitudinal direction relative to the spinal cord.

The use of such array is particularly preferred when stimulation of the cervical or the sacral spinal dorsal roots is desired.

The use of an Implantable Pulse Generator (IPG) able to simultaneously deliver independent current or voltage sources on multiple electrodes allows performing a multipolar stimulation. Such multipolar stimulation directs the stimulation field to the desired location by modulating the shape of the stimulating field with further current sources, thus enhancing spatial specificity of stimulation.

A further object of the present disclosure is a system for electrical neurostimulation of the spinal cord of a subject comprising:

a pulse generator, e.g., an Implantable Pulse Generator (IPG) able to simultaneously deliver independent current or voltage pulses on multiple electrodes; operatively connected with one or more multi-electrode arrays suitable to cover at least a portion of the spinal cord to selectively stimulate the spinal circuits and/or dorsal roots, wherein said IPG b) is operatively connected with said one or more multi-electrode arrays to provide a multipolar stimulation.

Neurostimulation can be used to control of nervous functions. Nervous functions can be, but are not limited to, locomotor functions, muscle stimulation, or the like. Possible applications can be, but are not limited to, restoring or enhancing of locomotor functions, pain treatment, restoring or enhancing immunological functions and/or the immune system, awareness or consciousness, restoring or enhancing bowel function, restoring or enhancing sexual function, restoring or enhancing cardiovascular function, restoring or enhancing bladder function, restoring or enhancing gastrointestinal function, especially function of sphincters in the gastrointestinal tract like the sphincters of the stomach.

This further system according to the present disclosure advantageously allows achieving higher muscle specificity by selectively stimulating dorsal roots of the spinal cord. Dorsal root multipolar stimulation is characterized by spatial selectivity.

The multi-electrode arrays preferably have the above mentioned configurations.

The use of such system allows targeting selectively the desired dorsal roots thus enhancing muscle specificity.

Another object of the present disclosure is the use of the system of the present disclosure for facilitating locomotor functions in a subject suffering from a neuromotor impairment and the related method for facilitating locomotor functions in said subject.

In an embodiment of the present disclosure, said neuromotor impairment is selected from a group consisting of partial or total paralysis of limbs. Said limb paralysis can be unilateral or bilateral. In particular, said neuromotor impairment is consequent to a spinal cord injury, an ischemic injury resulting from a stroke, or a neurodegenerative disease, for example, Parkinson's disease.

Another object of the present disclosure is a method for facilitating locomotor control in a subject in need thereof comprising the following steps:

a) acquiring signals from said subject;

b) transmitting said signals to a signal processing device;

c) calculating by means of said signal processing device electrical stimulation parameter settings;

d) providing said settings to an Implantable Pulse Generator (IPG) able to simultaneously deliver independent current or voltage pulses to one or more multiple electrode arrays, wherein said IPG provides said one or more multi-electrode arrays with a multipolar stimulation;

e) applying an electrical stimulation to said subject through said one or more multi-electrode arrays covering at least a portion of the spinal cord thereby providing a selective spatiotemporal stimulation of the spinal circuits and/or dorsal roots.

A further object of the present disclosure is a system for use in restoring voluntary control of locomotion in a subject suffering from a neuromotor impairment comprising:

a) a system for electrical stimulation of the spinal cord as above defined, and b) an apparatus selected from a group consisting of at least one of a treadmill or a robot-assisted body-weight support or a multidirectional trunk support system.

A further object of the present disclosure is a closed-loop system for electrical neurostimulation of the spinal cord of a subject for a fine control of the movement comprising:

a) a real-time monitoring component comprising sensors continuously acquiring feedback signals from said subject, operatively connected with b) a signal processing device receiving said feedback signals and operating real-time automatic control algorithms to elaborate electrical stimulation parameter settings, operatively connected with c) an Implantable Pulse Generator (IPG) receiving said stimulation parameter settings from said signal processing device b) with minimum delay and able to simultaneously deliver independent current or voltage pulses to multiple electrodes;

d) one or more multi-electrode arrays suitable to cover at least a portion of the spinal cord for applying to a subject a selective stimulation of the spinal circuits and/or dorsal roots, wherein said IPG provides said one or more multi-electrode arrays with a multipolar stimulation.

Such closed-loop system allows for a fine tuning and control of the movement; thanks to the feedback signals acquired from the subject, stimulation parameters, such as stimulation amplitude and frequency, can be continuously adjusted, thus allowing a fine control of the movements. For example, a fine control of the grade of extension/flexion of the lower limb during the gait phase can be achieved using such closed-loop system to adjust stimulation frequency; this allows a fine control of limb extension and foot trajectories.

Another object of the present disclosure is a method for facilitating standing and walking functions in a subject suffering from a neuromotor impairment comprising the following steps:

a) using the above mentioned closed-loop system for restoring voluntary control of locomotion;
b) providing to said subject a first epidural and/or subdural electrical stimulation with adjustable stimulation parameters using said multi-electrode array;
c) acquiring feedback signals from said subject, said signals being neural signals and/or signals providing features of motion of said subject;
d) transmitting said feedback signals to said signal processing device;
e) calculating by means of said signal processing device operating a Real Time Automatic Control Algorithm new electrical stimulation parameters;
f) providing to said subject a second epidural and/or subdural electrical stimulation with said new electrical stimulation parameters calculated in step e) using said multi-electrode array, and optionally g) administering to said subject before and/or during administration of said first and/or said second electrical stimulations a pharmaceutical composition comprising at least one agonist of monoaminergic receptors.

The present disclosure will be now described in detail also with reference to Figures and Examples.

DETAILED DESCRIPTION

Definitions

Within the frame of the present disclosure, the following definitions are provided.

"Apparatus": means a component comprising one or more devices cooperating to provide a more complex function. Examples of apparatuses are a computer, a monitoring component. An apparatus can also be integrated in a system.

"System": means an ensemble of one or more apparatuses and/or devices cooperating to provide a more complex function.

"Operatively connected" means a connection capable of carrying data flow between two or more input and/or output data ports. The connection can be of any suitable type, a wired or a wireless connection.

"Signal processing device": means any device capable of elaborating input signals and produce output signals. Said device can be a processor, incorporated in a more complex apparatus or system, such as for example a computer.

"Minimum delay" means close to real-time. For example, it means a delay comprising between about 0.1 and about 75.0 ms.

"Longitudinal", "lateral" and "medial" are used in their common medically accepted meanings, e.g., "longitudinal" refers to the axial direction of the spinal cord.

The term "transverse" includes both the lateral direction relative to the spinal cord and diagonal directions relative to the spinal cord but in either case the term "transverse" implies some crossing over a center line or point defined with respect to the spinal cord.

"Subject" means an animal provided with a spinal cord, in particular a mammal, more in particular a human.

A locomotion feature, or gait feature, is a kinematic parameter characterizing the gait cycle.

Figure 11:
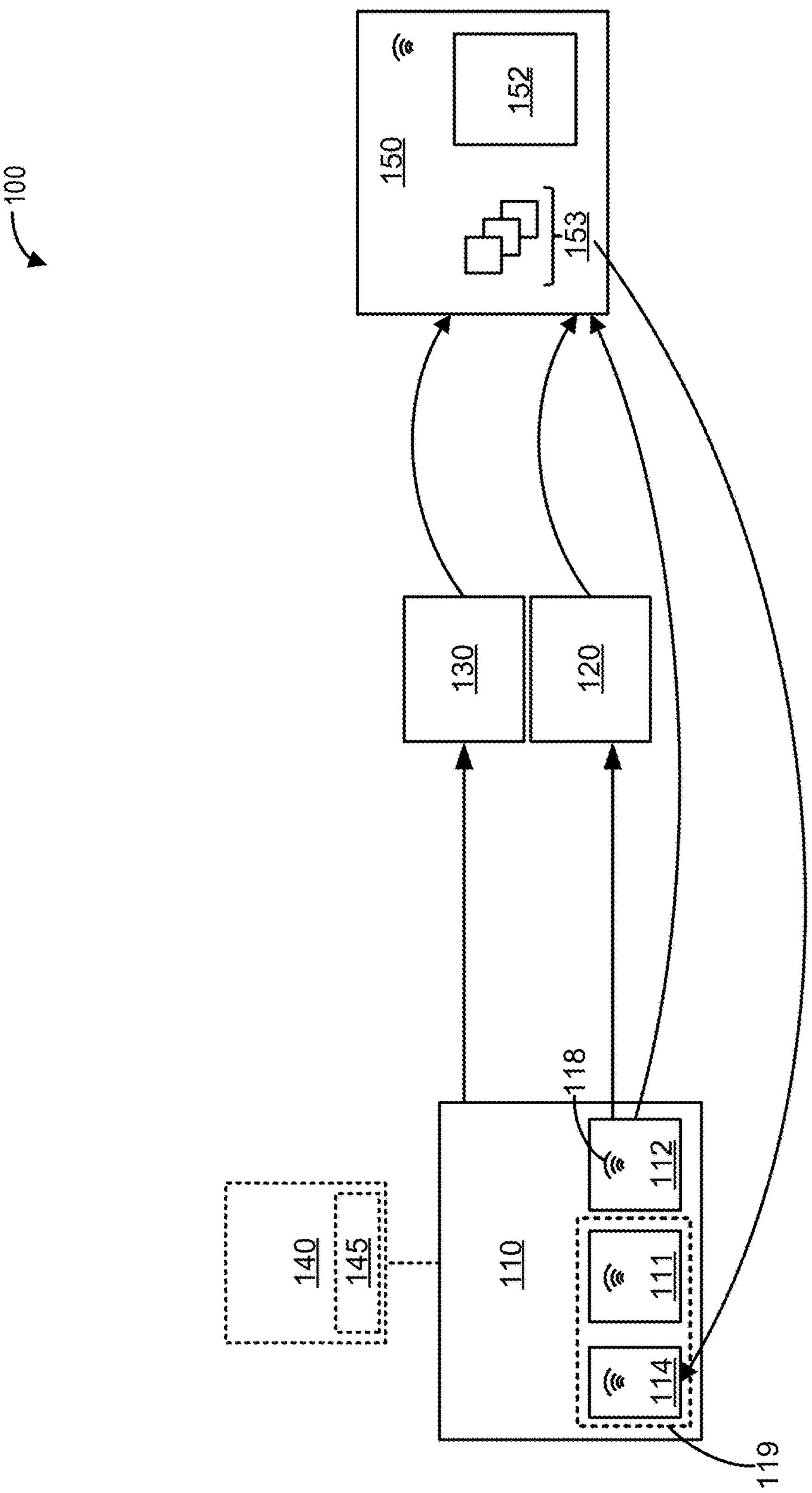
FIG. 11 shows a schematic diagram of an example system for electrical neurostimulation of a spinal cord, in accordance with an embodiment of the present disclosure.

Turning now to FIG. 11, a schematic diagram of an example neurostimulation system 100 for electrical neurostimulation of a spinal cord is shown. The neurostimulation system 100 includes a stimulation device 111 and a neurosensor 112. In the depicted embodiment, stimulation device 111 provides external sensory input to the central nervous system of a subject 110. For example, the stimulation device 111 may provide one or more of auditory, visual, tactile, thermal, chemical, optical, olfactory, gustatory, and electrical stimulation. It also may stimulate the subject to restore and/or enhance nervous functions. Nervous functions can be, but are not limited to, locomotor functions, muscle stimulation, or the like. Possible applications can be, but are not limited to, restoring or enhancing of locomotor functions, pain treatment, restoring or enhancing immunological functions and/or the immune system, awareness or consciousness, restoring or enhancing bowel function, restoring or enhancing sexual function, restoring or enhancing cardiovascular function, restoring or enhancing bladder function, restoring or enhancing gastrointestinal function, especially function of sphincters in the gastrointestinal tract like the sphincters of the stomach. As such, the stimulation device 111 may comprise one or more of a speaker, visual display screen, haptic stimulation inducer, heater, pharmaceutical delivery system, gas delivery system, taste delivery system, and electrical stimulation device.

In examples where the stimulation device 111 delivers electrical stimulation, the stimulation device 111 may be coupled to the subject 110 and may provide electrical stimulation to the spinal cord of subject 110. In particular, the stimulation device 111 may comprise a pulse generator, such as an implantable pulse generator (IPG), electrically coupled to one or more multi-electrode arrays. The one or more multi-electrode arrays may be placed epidurally or subdurally. For example, the one or more multi-electrode arrays of the stimulation device 111 may be implanted under vertebras L1-L4, and in particular, over the dorsal side of spinal segments ranging from L1 to S5 for enabling and/or facilitating movement of the lower limbs. Additionally or alternatively, the one or more multi-electrode arrays of the stimulation device 111 may be implanted under vertebras C2-T1, and, in particular, over the dorsal side of spinal segments ranging from C3 to T1 for enabling and/or facilitating movement of the upper limbs.

In particular, the neurostimulation system 100 may be used to provide stimulation (e.g., electrical stimulation) to the spinal cord in response to neural activity in the motor cortex of subject 110 in order to restore and/or control voluntary movement of the limbs and/or extremities, such as the legs, arms, hands, etc. In another example, the neurostimulation system 100 may be used to control a bionic robotic prosthetic.

Optionally, subject 110 may be coupled to a support apparatus 140, which may further include a motor movement eliciting device 145 (e.g., a treadmill) to assist in execution of motor movement by residual voluntary control of subject 110 or as elicited by the eliciting device 145. In one example, support apparatus 140 may be one or more of a robotic assistance device, a harness, a walker, physical assistance, an over-ground body weight support system, exoskeleton, etc. Thus, in examples where the eliciting device 145 comprises a treadmill, the support apparatus 140 may comprise a chest harness that holds the subject 110 in an upright position to elicit neural activity associated with locomotion and/or facilitate locomotion following stimulation. In this way, subject 110 is prompted to attempt a motor task so that volitional neural activity may be recorded, even in the absence of voluntary motor behavior. Further, eliciting device 145 may be used following spinal cord stimulation to facilitate locomotion of subject 110 in response to stimulation.

As subject 110 is attempting and/or engaged in a motor task, data congruent with attempts to move (e.g., neural activity recordings from a neurosensor 112) are sent to a signal processing device 150. If subject 110 is capable of executing, or partially executing, movements (e.g., engage some or all of the muscles involved in the attempted movement), the data may come in a form of kinematic data from one or more motion sensors, including a real-time monitoring component 120, a force place, an electromyogram recording system 130, a system of accelerometers affixed to subject 110, etc. Signal processing device 150 may also receive data from devices that instruct the subject 110 to move in a time-locked coordinated way, such as speakers delivering auditory cues, a video screen or lights delivering visual cues and/or creating a virtual reality environment, electrical stimulators, or any other device capable of delivering cues to subject 110. By recording neural activity following a prompt for the motor task, modulation of the neural responses of the subject to attempting the motor task may be used by algorithms 153 of signal processing device 150 to establish a model that maps neural activity to motor task attempts, which may be used to detect motor task attempts from neural activity. In this way, the motor task is employed to detect neural activity congruent with volitional movement execution.

During kinematic activity (e.g., motor movement), kinematic data for subject 110 is relayed to signal processing device 150. Signal processing device 150 receives kinematic activity signals from one or more of the real-time monitoring component 120 and the electromyogram recording system 130. The real-time monitoring component 120 records physical movements of the subject 110. For example, the real-time monitoring component 120 may comprise one or more of a video camera, an inertial measurement unit (IMU), an accelerometer, a gyroscope, a pressure sensor, a force sensor, an ultrasound detector, and an infrared sensor. The real-time monitoring component 120 may relay positional and/or movement data to the signal processing device 150 via a wired and/or wireless connection (e.g, via wireless signal 118). The movement data may comprise data encoding recorded physical movements of the subject 110. In examples where subject 110 is walking, the real-time monitoring component 120 records phases of the gait, such as stance and swing phases, and specific gait events such as foot off and foot strike. Thus, the real-time monitoring component 120 is used to record events and phases of the movement performed and/or aided by the movement eliciting device 145. However, in other examples, physical movement of the subject 110 may be measured via the electromyogram recording system 130. In still further examples, physical movement of the subject 110 may be measured via both the electromyogram recording system 130 and the real-time monitoring component 120. Thus, when included in the neurostimulation system 100, the electromyogram recording system 130 may be in communication with the signal processing device 150 via a wired and/or wireless connection for transmitting movement data to the signal processing device 150. In the description herein, the movement data may also be referred to as kinematic activity data. Electromyogram recording system 130 is coupled to subject 110 and records electrical activity at the muscles, which may be used to infer movement. Muscle activity during a motor task is then wirelessly transmitted from electromyogram 130 to signal processing device 150. In another embodiment, electromyogram recording system 130 may be wired to signal processing device 150 in order to relay muscle activity recordings.

The real-time monitoring component 120 records kinematic activity of subject 110 during movement eliciting device 145 use or over-ground walking. For example, real-time monitoring component 120 may be a video recording of subject 110 performing the motor task. In this way, output signals for both motor cortex activity and kinetic activity are relayed to signal processing device 150 during the motor task by neurosensor 112 and one or more of real-time monitoring component 120 and electromyogram 130, respectively.

Further, signal processing device 150 may be in wireless communication with the neurosensor 112 for receiving neural activity data therefrom. The neural activity data may comprise voltage output from the brain (e.g., motor cortex) of subject 110, in examples where the neurosensor 112 comprises a microelectrode array. In such examples, neurosensor 112 may be coupled to subject 110 and may wirelessly transmit neural activity data (e.g., motor cortex activity) to signal processing device 150 via wireless signal 118. However, in other examples, neurosensor 112 may be an electroencephalogram (EEG) or an intracranial electroencephalogram (iEEG). In further examples, neurosensor 112 may be a functional magnetic resonance imager (fMRI), electrocorticogram, near infrared spectroscopy system (NIRS), glass pipette electrode, one- or two-photon spectroscopy system with calcium indicators, neural activity recording system using voltage sensitive dyes, neural dust, tetrode array, wire electrodes, patch clamp electrodes, etc. In examples where the neurosensor 112 comprises a microelectrode array, the neurosensor 112 may be coupled to the motor cortex for monitoring motor cortex activity. Thus, the neurosensor 112 may transmit neural activity data, corresponding to electrical output from the motor cortex, to the signal processing device 150. En route to the signal processing device 150, the neural activity data measured by the neurosensor 112 may be digitized and packaged by a signal processor and transmitted to the signal processing device 150 over a local internet connection, such as via an Ethernet cable, via a standard communication protocol such as a user datagram protocol (UDP). However, it should be appreciated that other data transmission protocols (e.g., software) and transmission devices (e.g., hardware) may be implemented without departing from the scope of the present disclosure.

Neural and kinematic activity data is processed by algorithms 153 of signal processing device 150 to generate a model of currently executed motor movements using motor cortex activity. Thus, neural activity data and kinematic activity data are time synchronized to map the neural activity data to the corresponding kinematic activity data. In this way, neural activity patterns generated during execution of the motor movement may be identified by synchronizing the neural activity data with the kinematic activity data. The model of attempted motor movements using motor cortex activity created by the algorithms 153 is then used to adjust a stimulation protocol employed by a stimulation device system 119 to trigger spinal cord stimulation.

Signal processing device 150 may be communicatively coupled to various components of neurostimulation system 100 to carry out the control routines and actions described herein. For example, as shown in FIG. 11, signal processing device 150 may be a computer, including a processor unit, input/output ports, an electronic storage medium for executable programs and calibration values, random access memory, keep alive memory, and a data bus. Further, signal processing device 150 may take the form of one or more personal computers, server computers, tablet computers, network computing devices, mobile computing devices, mobile communication devices (for example, smart phone, smart watch, etc.), and/or other computing devices. As depicted, signal processing device 150 may receive input from a plurality of sensors, which may include user inputs and/or sensors (such as neural activity from neurosensor 112, muscle activity from electromyography recording system 153, kinetic activity from real-time monitoring component 120, etc.) and others. Signal processing device 150 may include one or more algorithms 153 for analyzing various signals received by signal processing device 150, including motor activity, muscle activity, and neural responses. Additionally, signal processing device 150 may include an interface 152. Furthermore, signal processing device 150 may communicate with various components of stimulation device system 119, which may include a stimulation controller 114. In some examples, the storage medium (e.g., memory) may be programmed with computer readable data representing instructions executable by the processor for performing the methods described below as well as other variants that are anticipated but not specifically listed.

Additionally, subject 110 may be physically coupled to stimulation device system 119. Stimulation device system 119 may include a stimulation controller 114 and stimulation device 111. In one embodiment, stimulation controller 114 and stimulation device 111 may be contained within a single housing and implanted subcutaneously. Stimulation controller 114 receives output for stimulation parameters for stimulation device 111 from signal processing device 150 and relays the stimulation parameters to stimulation device 111. In one example, stimulation controller 114 wirelessly receives Bluetooth signals from signal processing device 150 and relays stimulation commands to stimulation device 111 via, for example, transcutaneous telemetry. In the depicted embodiment, stimulation device 111 is an implantable pulse generator that electrically stimulates the spinal cord of subject 110 to control movement. For example, stimulation device 111 may be an implantable pulse generator that consists of an array of electrodes positioned epidurally or subdurally. Stimulation from the implantable pulse generator may be provided by passing current through one or more of the electrodes of the array for a duration. In one example, a stimulation event may consist of a burst of pulses from the implantable pulse generator. In another example, a stimulation event may consist of one or more of a single stimulation pulse. The single stimulation pulse may be a biphasic pulse, where the first pulse (e.g., phase) is a square wave pulse and the second pulse is an exponential decay pulse. For example, the stimulation event may be a 210 ms 50 Hz burst, which consists of nine single biphasic stimulation pulses of 50-2000 microseconds delivered 25 ms apart. In another embodiment, stimulation device 111 may employ photo- or vibrational stimulation of the spinal cord.

Components of the neurostimulation system 100 of FIG. 11 will be further described in the following sections. Then, experimental methods employing the example neurostimulation system 100 will be described. Finally, example experimental results obtained using the example neurostimulation system 100 will be described in order to illustrate advantages of using the embodiments described herein versus conventional neurostimulation systems.

Multi-Electrode Array

Figure 1:
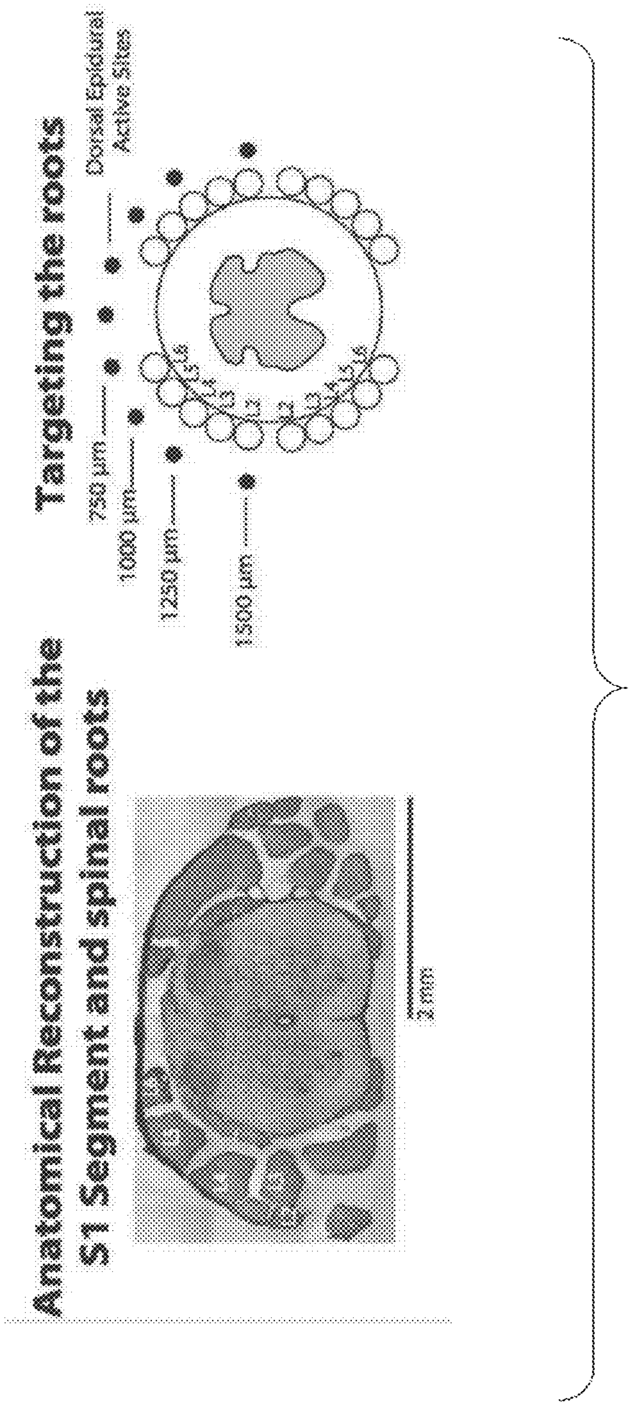
FIG. 1 shows a transversal representation of the sacral cord revealing the transversal topological organization of the longitudinal rootlets organized with rostral rootlets located more ventrally and caudal rootles located more dorsally. (Histology from rat, similar picture in humans can be found in (13))

Similar to humans (13), the rat lumbar spinal cord is surrounded by the dorsal roots that run longitudinally to the cord and show a specific topological organization at the L6/S1 segment. For example, FIG. 1 shows an anatomical reconstruction of the dorsal roots around the spinal cord at the S1 segment and how specific roots may be targeted by placing electrodes at specific dorsal epidural active sites. Roots innervating rostral segments are located more laterally while those innervating caudal segments are located medially, forming a left/right symmetric organization.

Therefore, multi-electrode arrays tailored to the anatomy of the dorsal roots should be used in a stimulation device (e.g., stimulation device 111 of FIG. 11).

According to the interested spinal segment that one wants to stimulate, multi-electrode arrays with different designs can be used.

It has been found that when the lumbar spinal roots (L2, L3, L4, L5 and S1) are targeted, a transversal positioning of the electrodes with respect to the spinal cord allows for a more selective stimulation of the dorsal roots.

Indeed, selective stimulation can be obtained by a transversal positioning of the electrodes that follows the topological organization of the rootlets around the lumbo-sacral levels.

Therefore, in an example embodiment, said multi-electrode array comprises:
- at least one portion comprising electrodes arranged in a direction transverse relative to the spinal cord and
- at least one portion comprising electrodes arranged in a longitudinal direction relative to the spinal cord.

In particular, for selective stimulation of the lumbar dorsal roots, the first portion of the array is positioned at the sacral level in a direction transverse relative to the spinal cord so as to effectively stimulate a spinal dorsal root associated with a lumbar spinal segment.

Such an array is preferably located under the T12 and L1 vertebrae.

Figure 6:
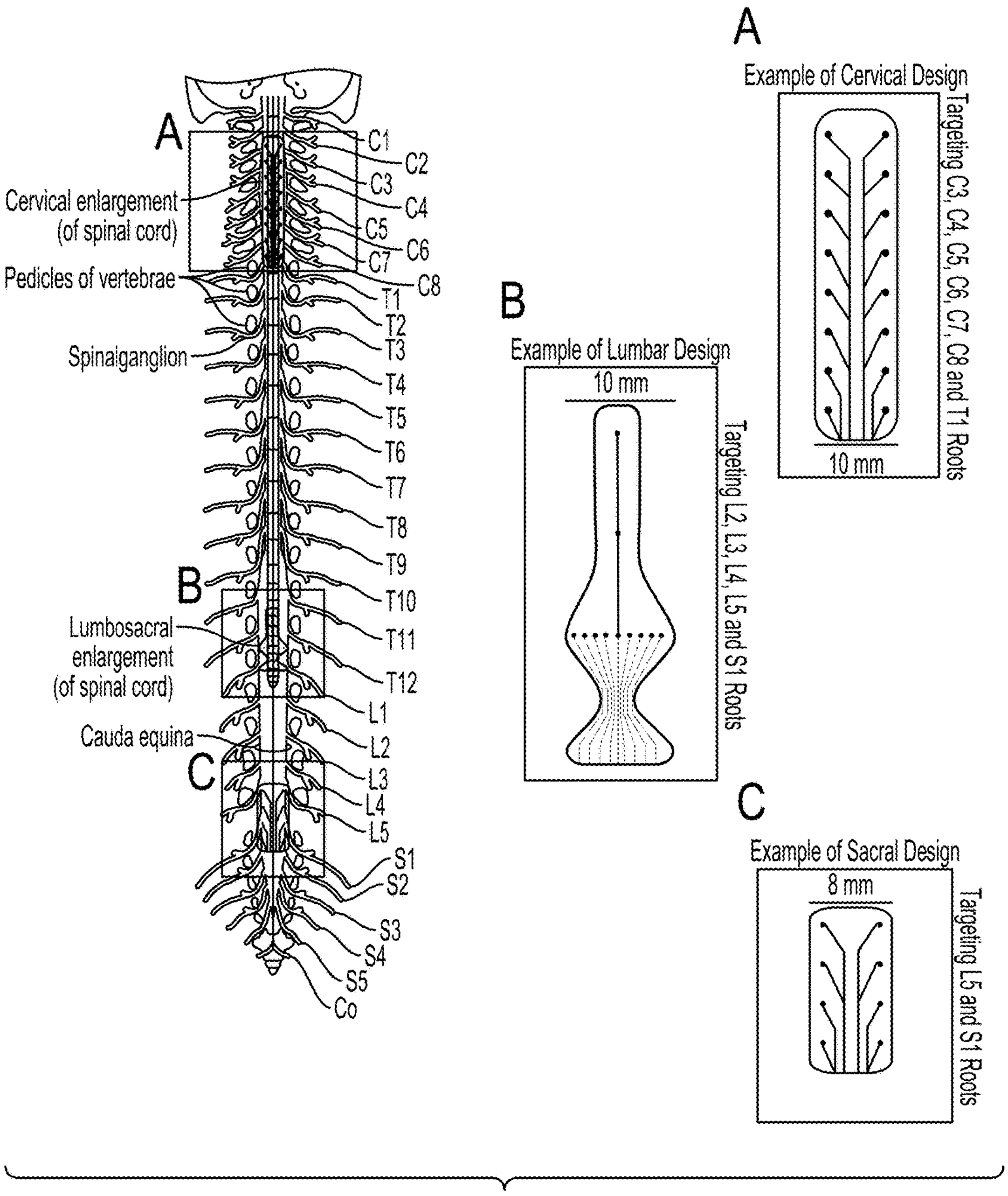
FIG. 6 shows possible designs of cervical, lumbar and sacral implants.

An exemplary embodiment is represented in FIG. 6B.

Preferably, said portion arranged transversally comprises a row comprising at least 5 electrodes.

In another exemplary embodiment, said multi-electrode array has between 3 and 9 transversal electrodes placed at a sacral level and between 2 and 6 midline electrodes placed at an L4 and L2 level. In a further exemplary embodiment, said array comprises 9 transversal electrodes and 2 midline electrodes See FIG. 4 for an exemplary representation of such a configuration.

The use of such array dramatically enhances the specificity of the stimulation since single dorsal rootlets can be targeted, reducing at the same time the recruitment of efferent fibers.

The midline electrodes provide tonic stimulation.

The transversally positioned electrodes provide tonic or multipolar stimulation.

According to the present disclosure, selectivity is achieved when the array is used with multipolar stimulation, as better explained below.

This electrode arrangement is particularly preferred for selective stimulation of the L4, L5, and S1 roots. Since these roots are very close to the central portion of the cord at the sacral level (see FIG. 3), selective, limb-specific stimulation is difficult to achieve with conventional means because of current spread in the cerebrospinal fluid that might cause contralateral stimulation. With said electrode configuration, selective stimulation of the L4 and L5 roots can be advantageously performed; consequently, selective stimulation of the Tibialis and Gastrocnemius muscles (innervated by the L4 and L5 roots) with no activation of the higher leg muscles is achieved.

In another example embodiment, said multi-electrode array comprises multiple electrodes arranged in two or more columns disposed in a longitudinal direction relative to the spinal cord.

The use of such array in the system of the present disclosure is particularly advantageous when targeting of sacral and cervical roots is desired. Indeed, in the sacral and cervical spinal portions, the roots have a left/right symmetrical organization, and they enter the cord at an angle comprised between 90 and 45 degrees for the cervical roots and between 45 and 60 degrees for the sacral roots.

The use of such longitudinal configuration of electrodes allows for selectively targeting only the desired dorsal roots, thus providing high muscle specificity.

For the targeting of the cervical roots (C3, C4, C5, C6, C7, C8 and T1 roots), the array is preferably implanted under the C2-T1 vertebrae. An exemplary embodiment is depicted in FIG. 6A.

For the targeting of the sacral roots (L5 and S1 roots), the array is preferably implanted under the L5-S1 vertebrae. An exemplary embodiment is depicted in FIG. 6C.

According to the present disclosure, the electrodes of said multi-electrode array can be set as cathodes (−), anodes (+), or High impedance NULL.

Preferred stimulation sites are lumbar and sacral sites for lower limb stimulation and cervical sites for upper-limb stimulation. Lower limb stimulation is applied, for example, for facilitating standing and walking in a subject; upper-limb stimulation is applied, for example, for facilitating reaching and grasping.

More than one multi-electrode array can be used together in the system of the present disclosure. Each array must be connected to the IPG of the stimulation device.

In an embodiment, two multi-electrode arrays with two different electrode configurations according to the embodiments described above are used together so as to obtain an even more selective stimulation of the interested root and, subsequently, muscle.

Locations of electrodes can be determined by the skilled person with general knowledge of neuro-anatomical features of a subject to be treated (e.g., subject 110 of FIG. 11).

Electrodes and arrays according to the present disclosure can be manufactured with conventional materials and methods according to the general knowledge in the field.

Preferably, they can be manufactured using the Polydimethylsiloxane (PDMS)-based technology (27).

The applicable stimulation frequency may be comprised between 5 and 120 Hz, preferably between 25 and 95 Hz.

Pulse-width is usually kept constant at a value comprised between 0.1 and 1.0 ms, preferably at 0.2 ms. Amplitude is usually set between about 0.1 and about 20.0 mA. Actual ranges and sub-ranges can vary from subject to subject.

Surgical methods to insert and stabilize the stimulation device into the epidural or subdural space are known in the art.

For example, laminectomies can be performed at vertebrae levels to create entry and exit points for the stimulation device. Electrophysiological testing can be performed intra-operatively to fine-tune positioning of electrodes.

Reference can be made, for example, to Courtine et al., 2009 (4) and van den Brand, 2012 (31).

The IPG—Implantable Pulse Stimulator

In the system of the present disclosure, one or more multi-electrode arrays may be operatively connected to an IPG in a stimulation device (e.g., stimulation device 111 of FIG. 11).

The IPG is a battery-powered micro-electronic device, implanted in the body, which delivers electrical stimulation.

Commercially available IPGs are suitable for the present disclosure.

An example of a commercially available IPG is the Eon Rechargeable IPG manufactured by Advanced Neuromodulation Systems, Inc.

In particular, the IPG of the present disclosure is able to deliver independent amounts of current to multiple electrodes simultaneously, thus controlling independent current sources.

Each electrode may be set to function as a cathode or an anode or set to a high impedance state for a given pulse.

Each electrode of the multi-electrode arrays of the present disclosure targets single rootlets with monopolar stimulation.

The positioning of the electrodes according to the present disclosure together with the IPG of the present disclosure allows the efficient use of multipolar stimulation strategies aiming at the selective stimulation of rootlets.

Therefore, the array of the present disclosure is used with a multipolar stimulation.

For multipolar stimulation, more than one electrode contact is used for stimulation at the same time.

The use of multipolar stimulation protocols leveraging the structure of the multi-electrode array allows to change and increase specificity of dorsal roots stimulation.

Multipolar stimulation protocols can be designed by the skilled in the art according to the common knowledge in the field, in particular regarding the innervation of the muscles by the spinal roots.

The use of an IPG comprising a neutral returning electrode as reference allows performing a referenced multipolar stimulation of electrodes by referencing the far field to the neutral ground voltage.

Selective recruitment of a spinal segment has been particularly difficult to achieve with classical protocols (12). The multi-electrode array coupled to an IPG with an independent source control for multipolar stimulation protocol is able to outperform classical approaches in terms of spatial specificity of spinal cord stimulation.

Independent source control of either voltage or current source and a common reference counter electrode allows switching from monopolar to multipolar stimulation with an undetermined number of cathodes or anodes that can be used to direct the stimulation field to the desired location and increase the stimulation specificity if required.

In an example embodiment, an IPG casing is set as a neutral referencing ground.

In another example embodiment, the IPG is set as a neutral referencing ground and the voltage/current values of the anode (+) and cathode (−) contacts are set independently. With this approach having at least 3 poles, a voltage generator of the IPG independently controls the voltage difference between the anode and the reference and the cathode and the reference, indirectly ensuring also the voltage difference between the anode and cathode, resulting in optimal and reliable multipolar stimulation.

For example, optionally referenced multipolar stimulation can be advantageously used to enhance single limb flexion or extension by stimulating and "shielding" specific paths.

For instance, a bipolar stimulation with a positive pole on one side and a negative pole on the midline (see, for example, FIG. 4) results in a contralateral extension due to the fact that the positive field will prevent the depolarization of fibers from the ipsilateral side, while the negative field will be constrained on the other side by the positive source engaging the more dorsal rootlets. An opposite combination will instead "shield" the contralateral side and stimulate the more ventral rootlets of the ipsilateral site.

Figure 4:
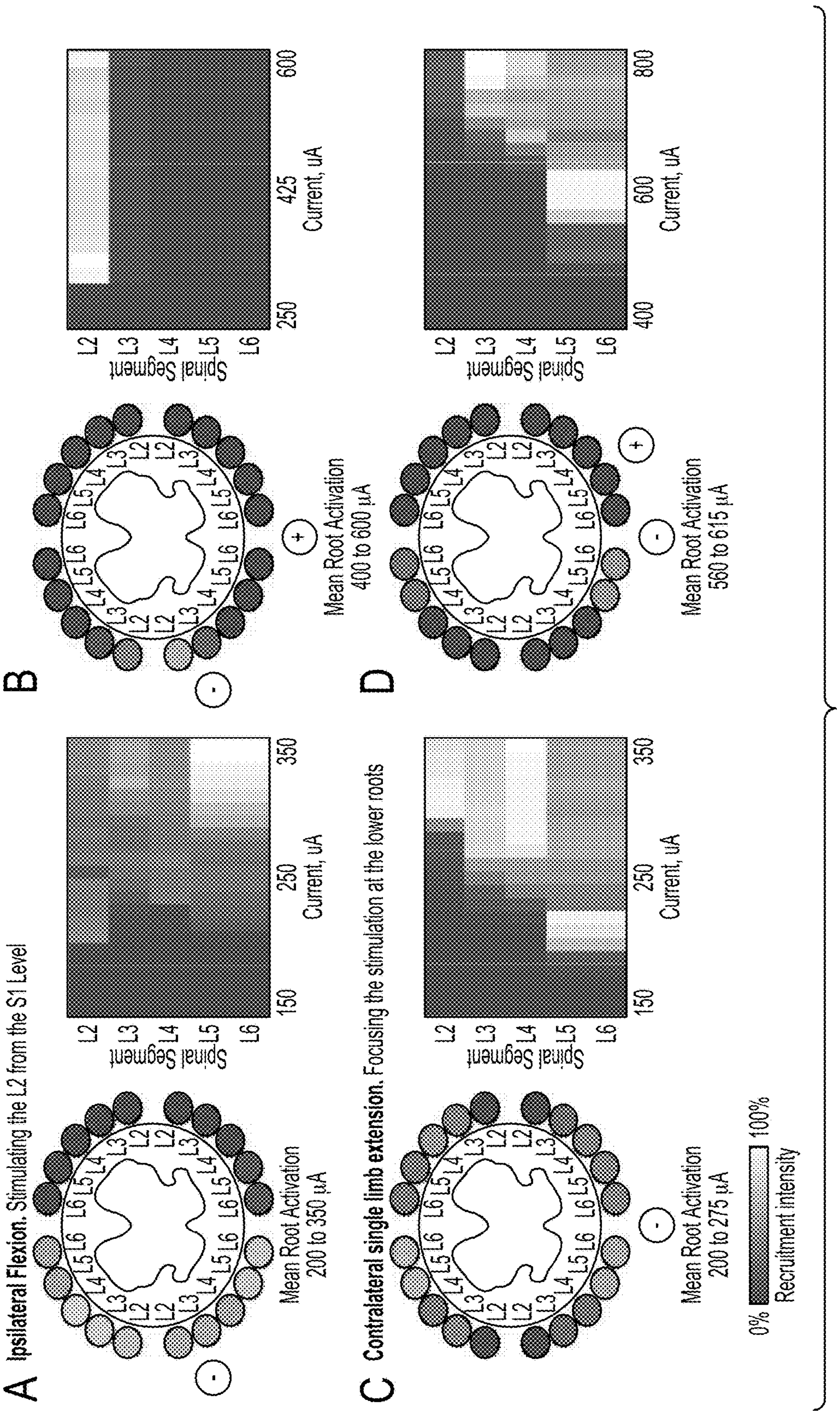
FIG. 4 shows experiments in rats revealing the improvement in specificity that can be achieved by using bipolar rather than single monopolar stimulation of the present disclosure in the transversal lumbar embodiment. Specific stimulation of the L2 root can be obtained by a balancing of the negative field in the E1 site (FIG. 3) with a positive field in the E5 site (see FIG. 3). The spinal maps show the recruitment intensity for each of the dorsal roots. Ventral roots (specular to the dorsal roots) are also represented. Targeting of the L5/L6 roots can instead be obtained by balancing the negative field of the E5 electrode with a positive field on the E7 contact. This generates selective recruitment of the left L5/L6 roots as opposed to bilateral spinal cord stimulation obtained with E5 monopolar stimulation.

An exemplary embodiment is represented in FIG. 4.

The application of an anodal source at site E5 together with stimulation of the E2 site restricts the activation to the L2 dorsal root, achieving single root specificity (FIG. 4B). This is due to the generation of a bipolar field that restricts the cathodic field to a small area around the cathode.

To selectively target the L5 and L6 left roots that innervate mainly extensor muscles of the ankle and foot (configuration named Contralateral single limb extension), an anodal source is applied at the site E7 to restrict the negative field applied to the E5 site to the roots closest to the midline from the left, thus achieving selective stimulation of left L5 and L6 roots (FIG. 4D).

In another exemplary embodiment, more than five electrodes are present so that a fine tuning of the exciting and inhibiting pathways is possible by moving the "excitatory" (e.g., the cathode) and the "shielding" (e.g., the anode) stimulation sites transversally on the different possible combinations.

Those skilled in the art are able to determine a suitable arrangement of the electrodes so as to obtain the desired stimulation and inhibition of the interested pathways using common knowledge in the field and the above-mentioned exemplary embodiments.

The IPG is coupled to a signal processing device (e.g., signal processing device 150 of FIG. 11) providing the IPG with stimulation parameter settings via, for example, a stimulation controller (e.g., stimulation controller 114 of FIG. 11).

Signal Processing Device

The signal processing device receives signals (neural, kinematic, and muscular, for example) from the subject as input and provides the stimulation controller with stimulation parameters (outputs) for stimulation of the subject with the IPG.

Signal-processing algorithms (e.g., algorithms 153 of FIG. 11) may be stored on a memory of the signal processing device and used to elaborate stimulation parameter settings using gait variables and parameters, as will be described further below. For example, stimulation parameters may be elaborated according to a specific gait phase or to gait parameters such as muscle activity, step height, and foot acceleration.

Preferably, each electrode may be triggered based on an automatic detection of gait events, which may be derived by the signal processing device using feature detection algorithms that use external signals. Such algorithms allow detecting gait events such as foot-strike or toe-off. Through these algorithms, the signal processing device may provide the stimulation controller with information regarding the turning on or off of specific electrodes in order to promote, for example, whole limb flexion and whole limb extension to increase muscle activity of relevant muscles and thus improve locomotor output.

Suitable triggering times may be obtained for each electrode through feature detection algorithms monitoring foot kinematics and deriving optimal gait events based on the timing within the gait cycle, as defined both by kinematic states and muscular activation. Preferably, said signal-processing algorithms may detect the timing of gait events based on a real-time tracking of limb kinematics. For example, a real-time monitoring component (e.g., real-time monitoring component 120 of FIG. 11) can be used to acquire information (signals) from the subject.

To optimize the timing of stimulation onset and end for each relevant electrode of the stimulation device, a comprehensive mapping that links the timing of stimulation with functional effects in the subject to be treated may be performed.

The acquired signals are neural signals (e.g., from neurosensor 112 of FIG. 11) and/or signals providing features of motion of the subject (e.g., from real-time monitoring component 120 of FIG. 11) and/or electromyography signals (e.g., from electromyography recording system 130 of FIG. 11).

In an embodiment, the real-time monitoring component detects the movements of the subject through, for example, a motion capture system, an accelerometer, or any other equivalent means. In another example embodiment, the real-time monitoring component is a motion capture system which comprises limb position markers. These markers are placed on the subject's limb(s) that is (are) stimulated. Typically, the markers are of a reflective type, meaning that they reflect infrared light emitted by cameras of the motion capture system, thus allowing their tracking, but other types can be used. Examples of other markers suitable for the present disclosure are optical systems, electromagnetic systems, ultrasonic systems, and combinations of systems suitably integrated by what is known as the "sensor fusion" method, a triangulation system using radio frequency antennae and inertial sensors. Marker positions of the subject may be acquired in real-time and associated to specific labels (for example, crest, hip, knee, ankle, and foot) according to a user-defined kinematic model that may be built on a per-subject basis for high accuracy tracking. Said model evaluates a set of rules that compares X, Y, and Z coordinates of each marker and derives which set of coordinates corresponds to which label. Said kinematic model thus matches 3D positions of the markers with the joint they are attached to. Marker positions can be, for example, crest, hip, knee, ankle, and foot.

Said set of rules operates in three steps. In a first step, it evaluates the mediolateral coordinates of the markers to distinguish between those related to the right and to the left limb, thus identifying two subsets. In a second step, for each one of these two subsets, top-down rules use vertical coordinates to distinguish crest (highest marker), a first couple that includes hip and knee (which are lower than crest), and a second couple that includes ankle and foot (which are the lowest two markers) as well as a center of rotation of the foot. Finally (third step), for each one of these two couples, forward coordinates help distinguish knee from hip (knee is more forward than hip) and foot from ankle (foot is more forward than ankle).

For example, a Vicon Kinematic System (Nexus) can be used as the real-time monitoring component. Other commercially available or custom-built systems are suitable for the present disclosure.

The acquired coordinates are then transmitted to the signal processing device.

In another embodiment, the real-time monitoring component acquires neural signals from the subject, for example, from a neurosensor (e.g., neurosensor 112 of FIG. 11) that may be in wired or wireless communication with the real-time monitoring component. Said neural signals may provide information about the locomotor or kinematic state and the neuronal activity of the subject, and the real-time monitoring component may transmit them to the signal processing device.

Neural signals provide information related to the gait cycle and may be used to control or refine the triggering of electrodes in real time, respectively substituting or cooperating with a kinematic-feedback algorithm. In particular, in connection with said algorithm, there may be a logical process of triggering stimulation protocols. Stimulation protocols may be triggered when the foot reaches a certain point in space during the gait cycle, for example, at the moment of foot off (right before clearing the ground), to support the swing phase. Therefore, stimulation is triggered by kinematic parameters. However, the precision of this detection will affect the subsequent kinematics. If a real-time loop is not short enough, stimulation may be triggered too late, and then the stimulation would fail to promote swing, affecting kinematics. At the next gait cycle, the foot may not reach the desired point required to trigger the stimulation. Thus, precision and fast communication is a critical feature of this system to ensure continuous stepping.

In an exemplary embodiment, electrode arrays implanted in the limb area of the sensorimotor cortex of a subject collect information about a locomotor intention of the subject. Using machine-learning approaches, this information can be decoded by the signal processing device and discriminated into two behavioral states, “rest” or “walk.” The decoded information is then transmitted to the stimulation controller, which switches ON or OFF the stimulation device so that the desired locomotor pattern is achieved.

With regard to machine-learning approaches, reference can be made to the review “Corticospinal neuroprostheses to restore locomotion after spinal cord injury,” by D. Borton, M. Bonizzato, J. Beauparlant, J. Digiovanna, E. M. Moraud, N. Wenger, P. Musienko, I. R. Minev, S. P. Lacour, J. d. R. Millán, S. Micera and G. Courtine published in Neuroscience Research, vol. 78, p. 21-29, 2014.

The signal processing device may execute a program comprising an automatic control algorithm that interfaces simultaneously with a Kinematic Data Stream and/or a Neural Data Stream, e.g., the data flow from the real-time monitoring component. The program and the algorithm may be in any programming language able to operate in real time; for example, it may be in C, C++, C#, or Simulink/xPC. The program may be compiled according to the general knowledge of the skilled in the art using custom-made or commercially available software, for example, TDT. Said program is programmed to detect foot-strike in real time and to determine electrical stimulation parameters during each gait-cycle.

In particular, the Neural Data Stream is the data flow from the neurosensor, while the Kinematic Data Stream is the data flow from the real-time monitoring component detecting the movements of the subject.

In an exemplary embodiment, signal-processing algorithms detect the timing of gait events based on real-time tracking of bilateral limb kinematics. For example, the continuous temporal sequence of gait events may be derived from the angular displacements of a specific joint, for example, a limb endpoint such as a foot, around its continuously updated center of rotation. This progression of the joint in space divulges the current timing of gait. A recording system may generate raw 3D positions of the markers, which may be imported into the C++ environment, for example, in real time. Further, a custom algorithm for online interpolation of missing markers through triangulation and relabeling of each marker to the appropriate joint landmark may be developed. All signals may be filtered online using least mean squares adaptive filters. A control logic of the stimulation controller may trigger individual electrodes based on trajectories of left and right limb endpoints. Triggering-events may be extracted for each electrode individually. Control algorithms may continuously calculate the angular trajectory of the joint around a virtual center of rotation in the sagittal plane. A change in on/off state of each electrode configuration may be triggered when the angular values cross user-defined thresholds that are previously optimized for each electrode and subject.

The algorithm calculates for each gait-cycle k the estimated position of the virtual center of rotation $\hat{C}_k$ derived from the trajectory $T_k$ of each joint in the sagittal plane as:

$$(x_c, y_c) = \left(x_{max}, \frac{1}{N}\sum_{j=1}^{N} y_j\right)$$

where $x_{max}$ is the x-coordinate at the point of highest step-height ($y_{max}$), and N is the number of data points recoded per gait cycle. In order to prevent jittering due to cycle-to-cycle variability, the estimate of the center of rotation may be iteratively updated at every gait cycle as:

$$\hat{C}_k=\hat{C}_{k-1}+\mu(C_{k-1}+\hat{C}_{k-1})$$

with an updating factor $\mu=0.2$. This factor may be adjusted according to specific subject needs.

This approach captures the natural alternation of stance and swing phases during gait despite intrinsic variability within and in-between gait cycles. This procedure is also inherently invariant to scaling and compliant to detect triggering-times with high fidelity compared to other methods that exhibit an increase in variability with deteriorated gait movements.

These control algorithms provide a flexible tool to study and implement phase-dependent modulation of a neuroprosthetic system (e.g., neurostimulation system 100 of FIG. 11) in real-time during gait.

Electrical stimulation with the system of the present disclosure may be performed together with the use of a support apparatus (e.g., support apparatus 140 of FIG. 11) selected from a group comprising a treadmill, a robot-assisted body-weight support, or a multidirectional trunk support system, for example.

In an example embodiment, said support apparatus is a robotic interface capable of evaluating, enabling, and training motor pattern generation and balance in subjects with neuromotor impairments. For a description of said robotic interface, reference can be made to the paper, "Versatile robotic interface to evaluate, enable and train locomotion and balance after neuromotor disorders" Dominici N, Keller U, Vallery H, Friedli L, van den Brand R, Starkey M L, Musienko P, Riener R, Nat Med. 2012 July; 18(7):1142-7. doi: 10.1038/nm.2845. Further reference can also be made to the paper of van den Brand R, Heutschi J, Barraud Q, DiGiovanna J, Bartholdi K, Huerlimann M, Friedli L, Vollenweider I, Moraud E M, Duis S, Dominici N, Micera S, Musienko P, Courtine G, "Restoring voluntary control of locomotion after paralyzing spinal cord injury", Science, 2012 Jun. 1; 336(6085):1182-5.

Reference can also be made to WO2013179230.

Also, before and/or during administration of electrical stimulations, a pharmaceutical composition comprising at least one agonist of monoaminergic receptors may be administered to the subject.

Indeed, in an example embodiment, the system of the present disclosure may be used in combination with a pharmacological treatment for further facilitating locomotor functions. In particular, the combination of the system with pharmacological treatment provides for a synergistic effect on locomotor functions. In particular, a pharmaceutical composition comprising at least one agonist of monoaminergic receptors, in particular to serotoninergic, dopaminergic, and adrenergic receptors, can be administered to the subject.

For example, a pharmaceutical composition comprising at least one molecule that selectively activates the α2c adrenergic receptor subtype and/or blocks the α2a adrenergic receptor subtype, such as disclosed in WO2013179230 and WO2015000800, can be used.

A serotonergic agonist may also be used. Preferably, said agonist is 8-OHDPAT. For example, a serotonergic replacement therapy combining the 5HT2A agonist quipazine and the 5HT1A/7 agonist 8-OHDPAT may be used.

Closed-Loop Stimulation

It was previously shown that modulation of stimulation amplitude and frequency leads to gradual adjustments of limb movements (7).

It has now been found that such modulation can be advantageously used in the system of the present disclosure to finely control the movement.

For example, it may enhance extension versus flexion components, leading to a control of limb extension during stance and foot trajectories during swing.

For an exemplary and detailed description of such a closed-loop system, reference can be made to WO2015063127 and to Wenger et al., 2014 (7).

Medical Uses

The system of the present disclosure may be used to facilitate locomotor functions in a subject suffering from an injured locomotor system, especially due to a neuromotor impairment. Therefore, the use of said system for facilitating locomotor functions in a subject suffering from a neuromotor impairment is an object of the present disclosure. In particular, said neuromotor impairment may be partial or total paralysis of limbs. Said neuromotor impairment may have been caused by a spinal cord injury, Parkinson's disease (PD), an ischemic injury resulting from a stroke, or a neuromotor disease such as, for example, Amyotrophic Lateral Sclerosis (ALS) or Multiple Sclerosis (MS).

For example, the device may be used to facilitate locomotor functions in a subject after spinal cord injury, Parkinson's disease (PD), or stroke.

The present disclosure will be now illustrated by the following examples.

EXAMPLES

Methods

Animals and Animal Care

All procedures and surgeries were approved by the Veterinarian Office Vaud, Switzerland. The experiments were conducted on adult female Lewis rats (200 g body weight, Centre d'Elevage R. Janvier). Rats were housed individually on a 12-h light-dark cycle, with access to food and water ad libitum.

Surgical Procedures and Post-Surgical Care

Procedures have been described in detail previously (4, 31). All interventions were performed under general anesthesia and aseptic conditions. Briefly, in one experiment, a pair of Teflon-coated stainless steel wires was inserted into the Medial Gastrocnemius and Tibialis Anterior muscles of both hindlimbs, while in the bipolar configuration experiments, the Gluteus medialis and Ilio Psoas muscle were also implanted bilaterally. Electrodes were created by removing a small part (~1 mm notch) of insulation. Briefly, 2 partial laminectomies were performed at vertebrae levels L3-L4 and T12-T13 to create entry and exit points for the implant. The implant was gently pulled above the dura mater using a surgical suture. Electrophysiological testing was performed intra-operatively to fine-tune positioning of electrodes. The connector of the implant was secured into a protective cage and plastered using freshly mixed dental cement on top of the L3-L4 vertebra. A common ground wire serving as counter electrode was inserted subcutaneously over the right shoulder.

Micro-Computed Tomography

Repeated imaging of spinal implants in vivo was conducted using the micro-computed tomography scanner Skyscan 1076 (Bruker μCT). Scanner settings were adjusted to avoid artifacts induced by metallic parts of the vertebral orthosis (0.5-1 mm aluminum filter, voltage 70-100 kV, current 100-140 μA, exposure time 120-160 ms, rotation step 0.5 deg). The resulting projection images were reconstructed into 3D renderings using NRecon and GPURecon Server (Bruker μCT). Rats were kept under isoflurane anesthesia during the scan to reduce motion artifacts. Segmentation and 3D models were constructed with Amira® (FEI Vizualisation Sciences Group).

Rats: Recruitment Curves

EES-evoked motor responses were recorded during bipedal standing in a support harness with 80% body weight support. Rectangular pulses (0.2-ms duration) were delivered at 0.5 Hz through the implanted electrodes (12). The intensity of the electrical stimulation was increased progressively until saturation of responses was reached. EES-evoked motor potentials were recorded in the implanted muscles. Electromyography (EMG) signals (12.207 kHz) were amplified, filtered (1-5,000-Hz bandpass), and stored for off-line analysis. The onset latency and peak amplitude of the different components in compound action potentials were determined through custom-made software in Matlab. Acute bipolar experiments were performed under urethane (1 g/kg, i.p.) anesthesia.

Roots and Motoneuron Activation Maps

To visualize a roots and motoneuron activation map, electromyographic signals were mapped onto the rostrocaudal distribution of the motorpools [21]. This approach provides an interpretation of the motoneuron activation at a segmental level rather than at the individual muscle level. The maps were constructed by adding up the contributions of each muscle to the total activity at each spinal segment. The motor output pattern of each spinal segment Si was estimated by the following equation:

$$S_i = \frac{\sum_{j=1}^{ni}\left(\frac{MNij}{MNj}\right)\cdot EMGj}{\sum_{j=1}^{ni}\left(\frac{MNij}{MNj}\right)}$$

where ni is the number of muscles located in the i-th segment, EMGj represents the normalized activity of the j-th muscle, MNij is the number of motor neurons related to muscle j and located at the segment i, MNj is the total number of motor neurons for the muscle j, Ni is the number of muscles innervated by the i-th spinal segment.

Human: Recruitment Curves

EES-evoked motor responses were recorded during standard intra-operative routine electrophysiology measurements. Rectangular balanced biphasic pulses (0.3-0.5 ms duration) were delivered at 0.5 Hz through monopolar electrodes (12) located over the cervical roots C7 and C8 in the epidural space. The intensity of the electrical stimulation was increased progressively until saturation of responses was reached. Stimulus-triggered EES-evoked motor potentials were recorded in the implanted muscles. EMG signals (10 kHz) were amplified, filtered (1-2000-Hz bandpass), and stored for off-line analysis. The onset latency and peak amplitude of the different components in compound action potentials were determined through custom-made software in Matlab.

Real-Time Monitoring Platform

The real-time monitoring and control platform was implemented within a multi-threaded C++ code (Visual Studio 2010, Microsoft) running on a quad core Microsoft Windows 7 computer. Stimulation patterns were applied via an RZ5 processing unit (Tucker-Davis Technologies) connected to an MS16 Stimulus Isolator (Tucker-Davis Technologies). The integrated Vicon recording system generated raw 3D positions of the markers, which were imported into the C++ environment in (soft) real-time via Ethernet using the DataStream SDK software. We developed a custom algorithm for online interpolation of missing markers through triangulation and relabeling of each marker to the appropriate joint landmark. All signals were filtered online using least mean squares adaptive filters.

The control logic triggered individual electrodes based on trajectories of left and right hindlimb endpoints of a rat. Triggering-events were extracted for each electrode individually. Control algorithms continuously calculated the angular trajectory of a foot around a virtual center of rotation in the sagittal plane. The change in on/off state of each electrode configuration was triggered when the angular values crossed user-defined thresholds that were previously optimized for each electrode and rat during mapping experiments.

The algorithm calculated for each gait-cycle k the estimated position of the virtual center of rotation $\hat{C}_k$ derived from the trajectory $T_k$ of each foot in the sagittal plane as:

$$(x_c, y_c) = \left(x_{max}, \frac{1}{N}\sum_{j=1}^{N} y_j\right)$$

where $x_{max}$ is the x-coordinate at the point of highest step-height ($y_{max}$), and N is the number of data-points recoded per gait cycle. In order to prevent jittering due to cycle-to-cycle variability, the estimate of the center of rotation was iteratively updated at every gait cycle as:

$$\hat{C}_k = \hat{C}_{k-1} + \mu(C_{k-1} - \hat{C}_{k-1})$$

with an updating factor $\mu=0.2$. This approach captured the natural alternation of stance and swing phases during gait despite intrinsic variability within and in-between gait cycles. This procedure was also inherently invariant to scaling and compliant enough to detect triggering-times with high fidelity compared to other methods that exhibit an increase in variability with deteriorated gait movements. These control algorithms provide a flexible tool to study and implement phase-dependent modulation of a neuroprosthetic system in real-time during gait.

To evaluate the delay in the processing time of this loop, we simulated an input and recorded the time necessary to adapt the stimulation parameters. This delay included the processing of video recordings by the motion capture system (e.g., real-time monitoring component 120 of FIG. 11), the transfer of video data via Ethernet to a real-time control computer (e.g., signal processing device 150 of FIG. 11), the processing of these video data using dedicated libraries, the changes in parameters of the stimulus isolator, and the delivery of a modified stimulation pulse through a plug mounted on the head of the rat. We sent concomitant pulses at opposite ends of the loop and calculated the discrepancy between both signals after each iteration for more than 100 successive cycles. The computed delays remained below 20 ms. Custom-developed C++ and TDT (Tucker-Davis Technologies) codes will be made available through material transfer agreement upon request to G.C.

Behavioral Recordings

Rats were recorded under two conditions. First, bipedal locomotion was recorded on a treadmill (e.g., movement eliciting device 145 of FIG. 11) while a robotic bodyweight support system (e.g., support apparatus 140 of FIG. 11) provided optimal support against the direction of gravity and prevented lateral falls. Second, quadrupedal locomotion was recorded along a straight runway with a flat surface and along a staircase that combined a succession of 4 steps, as described previously ([32]). All of the experimental conditions within and between recording sessions were randomized.

Spatiotemporal Neuromodulation in Rats with Complete SCI

Electrochemical stimulation protocols were selected based on an extensive amount of previous studies in rats with complete and incomplete SCI [5, 7]. A serotonergic replacement therapy used during training was administered systemically prior to testing. After a few minutes, monopolar electrical stimulation currents were delivered between relevant electrodes of the implants and an indifferent ground located subcutaneously. The intensity of electrical spinal cord stimulation was tuned (40 Hz, 20-200 μA, biphasic rectangular pulses, 0.2 ms duration) to obtain optimal stepping visually.

To optimize the timing of stimulation onset and end for each relevant electrode of the spinal implant (e.g, stimulation device 111 of FIG. 11), we performed a comprehensive mapping that linked the timing of stimulation with functional effects in rats with complete transection of the thoracic spinal cord. For each rat (n=5), the duration of the gait cycle (800±156 ms, SD) was normalized and then divided into 10 equal bins that served as triggering events to turn the stimulation on or off. For electrodes targeting extensors versus flexors, the stimulation was turned on or off over the entire range of bins. A total of 10 steps were usually recorded for each electrode and bin. Temporal structure was optimized based on the modulation of a few gait parameters that characterized the expected effects of the stimulation. For example, the gait parameters included the ability to lift the foot from the ground, as measured by step height. The temporal structure was considered optimized when stimulation produced a satisfactory step height. The timing of the electrodes targeting the extensors was driven by an amplitude of ankle extensor muscle activity, an amount of vertical ground reaction forces, and an intensity and amount of foot acceleration at push off. The timing of the electrodes targeting the flexors was driven by an amplitude of flexor muscle activity, an amount of foot dragging, step height, and an intensity and orientation of foot acceleration at swing onset. These parameters were weighted equally for identification of the optimal temporal structure for both extension and flection selective electrodes or combinations of electrodes.

After optimization of the temporal structure, the ability of spatiotemporal neuromodulation to mediate superior facilitation of locomotion compared to continuous neuromodulation was tested in the same rats during bipedal locomotion on a treadmill. A total of 10 to 20 successive steps were recorded during continuous neuromodulation (40 Hz, 20-200 μA, biphasic rectangular pulses, 0.2 ms duration) applied through electrodes located over the midline of spinal segments L2/L3 and S1 (conventional protocols) and through spatially selective electrodes located on the lateral aspect of the same segments. Locomotor performance was compared with neuromodulation applied through the same spatially selective lateral electrodes with the identified temporal structure. The amount of robot-assisted bodyweight support was maintained constant across conditions. The amplitude of stimulation was adjusted for each condition. The amplitudes optimal for spatiotemporal neuromodulation could not be used for continuous neuromodulation since these values led to diminished performances and could occasionally block hindlimb movements.

The maximum weight bearing capacity of each rat with contusion SCI was tested under continuous neuromodulation and spatiotemporal neuromodulation around 3 weeks post-SCI. From an optimal vertical weight support condition, the amount of assistance was decreased by 5% increments after each sequence of 10 successful steps until the rats collapsed. Kinematic and muscle activity was recorded throughout these evaluations.

The endurance of rats with contusion SCI was recorded on two different days that were randomized across animals, around 3 weeks post-SCI. From an optimal vertical weight support condition, rats stepped with continuous neuromodulation or spatiotemporal neuromodulation until they collapsed onto the treadmill. Concomitant kinematic recordings were used to measure the step height of each step.

Rats with contusion SCI were evaluated during quadrupedal locomotion at 2 months post-SCI, when functional recovery had plateaued [5]. Rats performed 10 successive trials without stimulation with the serotoninergic replacement therapy and spatiotemporal neuromodulation, both along the runway and staircases. Bilateral hindlimb and trunk kinematics were recorded during these trials. The percent of tumbles, touches, and passes over the steps was computed using video recordings. Tumbles were defined as dragging throughout the execution over the step, whereas touches characterized gait cycles during which the paw entered into contact with the steps but passed it successfully. The events were classified as "pass" when the paw had no contact with the step during the entire swing phase.

Statistical Analysis

All the computed parameters were quantified and compared between tested groups, unless otherwise specified. Statistics were performed on averaged values per rat. All data are reported as mean values +/−SEM, unless specified otherwise. Significance was analyzed using a paired Student's t-test, ANOVA or repeated measures ANOVA when data were distributed normally. Post hoc comparisons were performed using the Kruskal-Wallis test. The non-parametric Mann-Whitney test was used for comparisons with less than 6 rats.

Results

Spatial Specificity

Example 1

Design of Selective Interfaces for Lumbar, Sacral, and Cervical Root Stimulation We found that selective dorsal root stimulation has superior performances in terms of root specificity compared to classical approaches. Therefore, we tailored the design of a lumbar epidural array to the S1 spinal segments of rats.

Similar to humans (13), the rat lumbar spinal cord is surrounded by the dorsal roots (FIG. 1) that run longitudinally to the cord and show a specific topological organization at the L6/S1 segment. Dorsal roots are formed by ensembles of sensory afferents, including large myelinated proprioceptive and cutaneous fibers that are recruited by Spinal Cord Epidural Stimulation. At the sacral level, in mammals, the roots are organized in longitudinal substructures that surround the cord up to the entry point of each rootlet. A transversal representation of the sacral cord reveals the transversal topological organization of the longitudinal rootlets organized with rostral rootlets located more ventrally and caudal rootles located more dorsally. Selective stimulation has been obtained by a transversal positioning of the active sites of an Epidural interface that follows the topological organization of the rootlets around the sacral levels. (Histology from rat, similar picture in humans can be found in (13))

Roots innervating rostral segments are located more laterally while those innervating caudal segments are located medially, forming a left/right symmetric organization.

We found that a neural interface with electrodes surrounding the dorsal aspect of the S1 segment allows for specific root activation.

We designed and implemented (FIG. 2) such an interface using the PDMS-based technology presented in [27]. Stable implantation in rats was achieved, and micro-CT scans acquired on the animals 1 week post injury confirmed the correct placement of the interface with active sites surrounding the dorsal aspect of the S1 segment (FIG. 2).

Example 2

Validation of Lumbar Root Stimulation in Rats: Monopolar Specificity

Figure 2:
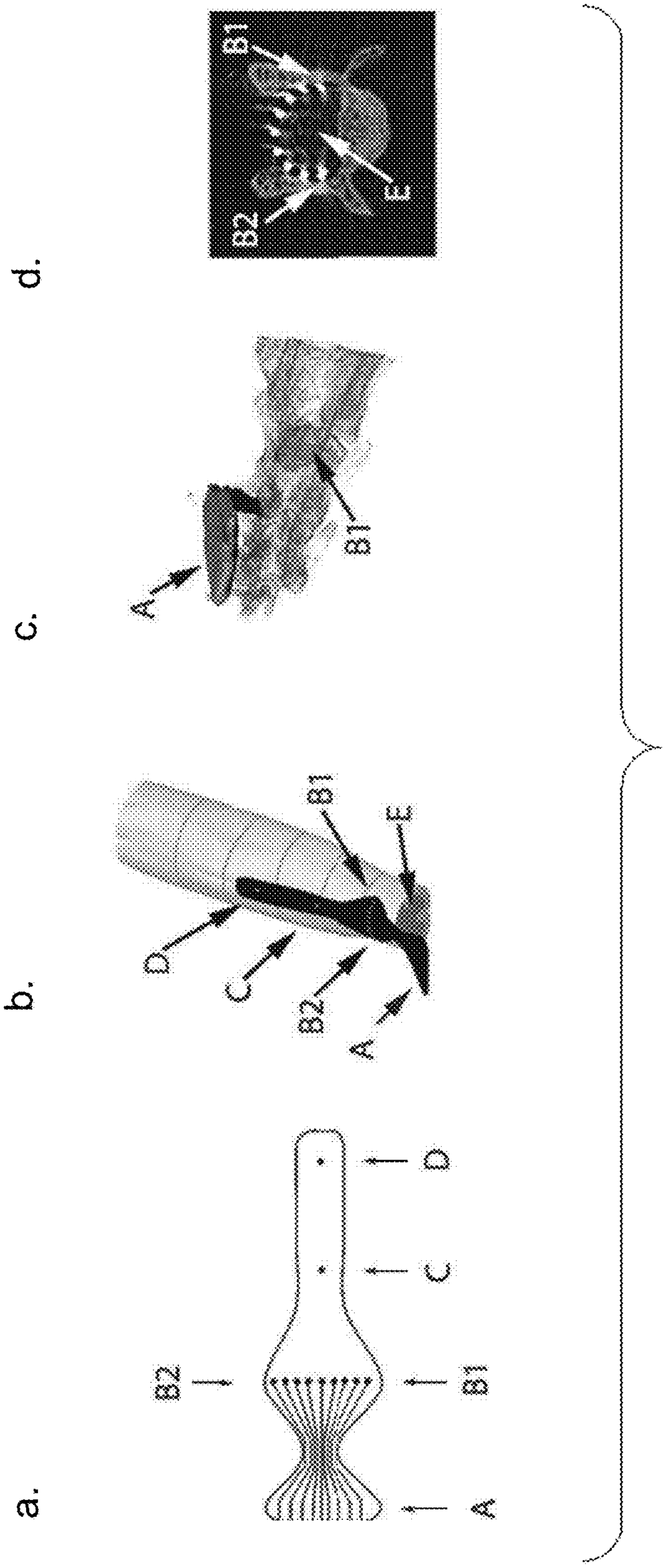
FIG. 2 shows a possible design and implantation procedure of an epidural electrode for selective root stimulation. This embodiment of the present disclosure depicts a transversal configuration for optimal stimulation of the lumbar dorsal roots. In this embodiment a row of electrodes (B1-B2) is located at the sacral level. Micro CT scans from experimental rats (3D reconstruction and transversal section of the S1 segment (E)) shows successful implantation in chronic animal models. The connector A is located outside the Epidural Space. In C and D midline active sites are represented.

We implanted our stimulation device (e.g., stimulation device 111 of FIG. 11), which included a multi-electrode array for selective dorsal root stimulation, over the S1 spinal segment below the L2 vertebra in rats (FIG. 2 and FIGS. 3A and 3B). The electrodes were disposed transversally over the dorsal aspect of the S1 spinal segment. Animals were implanted with chronic EMG electrodes in ankle flexor and extensor muscles of both limbs (Tibialis Anterior and Medial Gastrocnemius, TA and MG respectively) to record muscle activity (e.g., with electromyogram recording system 130 of FIG. 11).

Figure 3:
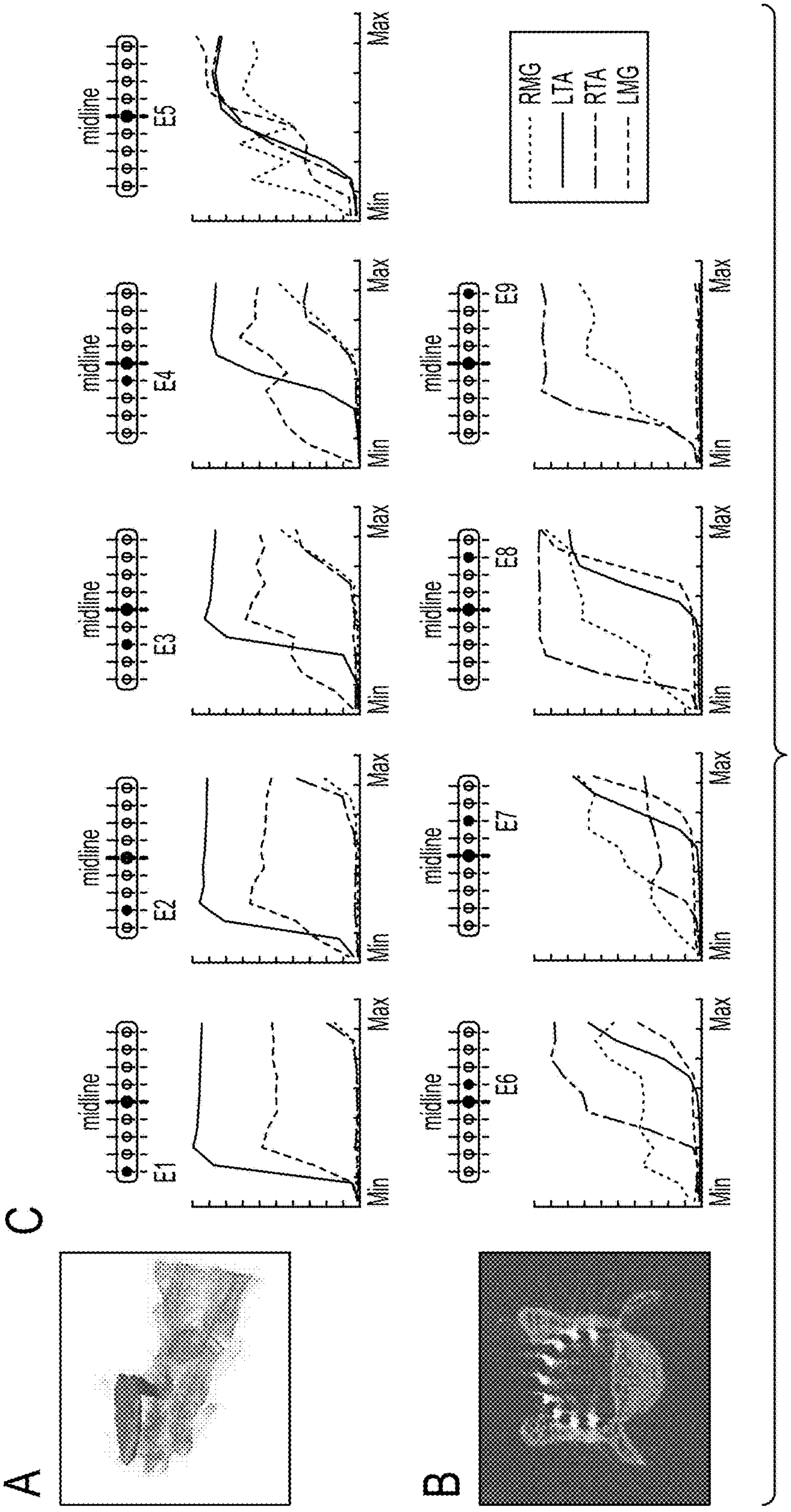
FIG. 3 shows chronic experiments in experimental animals (rats), which show the feasibility and specificity of an embodiment of the present disclosure. Specifically a transversal sacral embodiment has been implanted (A, B, and FIG. 4). Single site referenced stimulation of the interface from its left-most to right-most electrode reveals a progressive recruitment of the rootlets switching from complete left specificity to complete right specificity. Single rootlet stimulation can also be seen in the comparison between E1 vs E4 site and E9 vs E6 site. Relative Threshold between the Tibialis (TA) and the Gastrocnemius (MG) muscle respectively for the left and right side (L and R). In E1 and E9 TA has lower threshold than MG, and in E4 and E6 MG has a lower threshold than TA. Rootlets targeting the TA are located more ventrally while rootlets targeting the MG are located more dorsally, thus more dorsal sites (E4 and E6) are able to specifically target MG rootlets. Ventral sites (E1 and E9) can instead target more ventral rootlets.

We performed recruitment curves of muscle evoked potential by stimulating the animals with single pulse EES at increasing current amplitudes through each of the 9 active sites (FIG. 3). Results show the progression of the muscle recruitment from the leftmost (site E1) to the rightmost (site E9) active site. Stimulation of the E1 site induces clear activation of the left TA and left MG (LTA and LMG) with high limb specificity. The threshold for the TA is lower than the MG, which reflects the fact that the TA is innervated by more rostral segments than the MG [12]. Therefore, dorsal roots innervating the TA are more lateral, while those innervating the MG are more medial/dorsal. Results show that by following the transversal dorsal organization of the roots, stimulation of each single site with monopolar stimulation progressively induces a switch in the activation order of the MG/TA when moving more medially. Complete symmetry between left and right and lower MG thresholds is then reached at the midline site (E5). Finally, a symmetric recruitment of muscles for the right leg is achieved with the right sites E6 to E9. These results prove that selective root stimulation achieves high muscle specificity even with monopolar stimulation thanks to our newly developed multi-electrode array that is tailored to the anatomy of the dorsal roots. Our strategy of targeting dorsal roots shows superior specificity when compared to classical approaches in rodents, especially with respect to flexor/extensor specificity [12, 16].

Example 3

Validation of Lumbar Root Stimulation in Rats: Bipolar Specificity

After experimental validation of selective dorsal root stimulation with monopolar electrode configurations, we exploited the design of our multi-electrode array for multipolar stimulation of the dorsal roots.

Multipolar stimulation can indeed increase specificity by modulating the shape of the stimulating field (cathodic) with anodic current sources.

We found that our transversal multi-electrode array can be used with multipolar stimulation patterns that aim at restricting the transversal diffusion of the cathodic field in order to increase root specificity.

For this, we connected our multi-electrode array with a pulse generator that controlled independent current sources and featured a common return electrode serving as a reference that was placed subcutaneously over the right shoulder.

First, we sought to selectively target the L2 root, which is known to innervate mainly hip flexor muscles [28] that have an important role in the initiation of locomotion. We termed this configuration Ipsilateral Flection. FIG. 4 shows an idealized representation of the S1 segment with both ventral and dorsal roots indicated by circles surrounding the cord. Ventral roots are located ventrally (top) and dorsal roots surround the dorsal part of the segment (bottom). Single pulse stimulation at increasing amplitude shows that stimulation of the site E2 (see FIG. 3) generates recruitment of the left roots; however, both ventral and dorsal roots are stimulated (FIG. 4A). The application of an anodal source at site E5 (see FIG. 3) restricts activation to the L2 dorsal root, achieving single root specificity (FIG. 4B). This is due to the generation of a bipolar field that restricts the cathodic field to a small area around the cathode.

Second, we sought to selectively target the L5 and L6 left roots that innervate mainly extensor muscles of the ankle and foot. We termed this configuration Contralateral single limb extension. We achieved selective stimulation of L5 and L6 roots only. While stimulating at the E5 site, both left and right L5 and L6 roots were mainly recruited (FIG. 4C). The application of an anodal source at the site E7 restricted the negative field to the roots closest to the midline from the left, achieving selective stimulation of left L5 and L6 roots (FIG. 4D).

Selective recruitment of a caudal segment has been particularly difficult to achieve with classical protocols [12]. Thus, our multi-electrode array coupled to an independent source control with a common reference for a multipolar stimulation protocol is able to outperform classical approaches in terms of spatial specificity of spinal cord stimulation.

These results also prove the ability to change and increase the specificity of dorsal roots stimulation with multipolar stimulation protocols that leverage the structure of our multi-electrode array. Independent source control of either voltage or current source and a common reference counter electrode was pivotal for these results since it allows switching from monopolar to multipolar stimulation with an undetermined number of cathodes or anodes that can be used to direct the stimulation field to the desired location and increase the stimulation specificity if required.

Example 4

Validation of Cervical Root Stimulation in Humans

We found that selective dorsal root stimulation with EES can be used to induce specific muscle responses in the limbs that constitute the basic mechanisms behind the restoration of motion after spinal cord injury.

We first tested this in rats while stimulating the lumbar spinal cord.

Second, we tested whether selective dorsal root stimulation could also produce specific muscle activity in the upper limb of humans.

This test allows the generalization of our findings to upper limb movement disorders.

For this, we performed intra-operative electrophysiological tests in two patients that were receiving a surgery for a cervical disc hernia.

Figure 5:
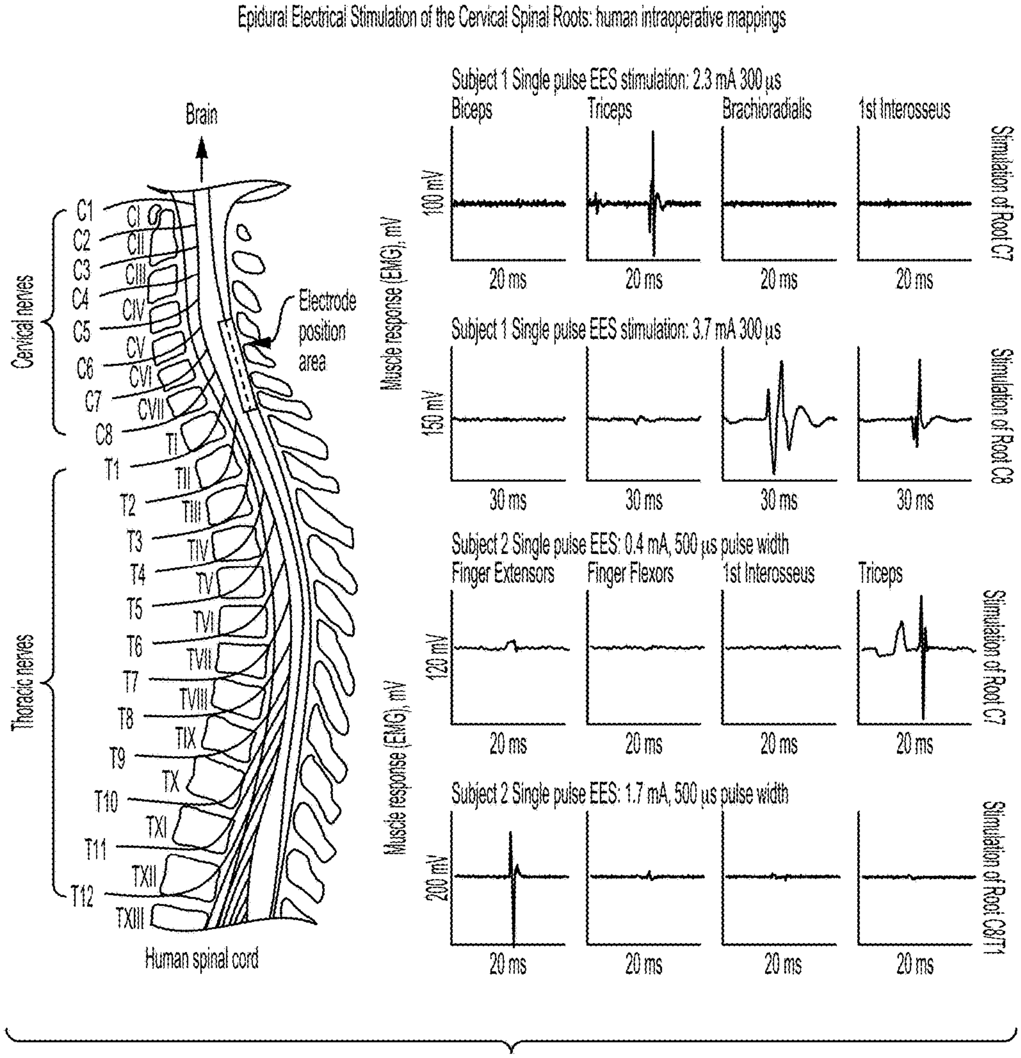
FIG. 5 shows intra-operative tests of human subjects revealing the specificity of another possible embodiment of the present disclosure. Selective referenced monopolar stimulation of cervical dorsal roots (C7 or C8) induces specific responses in the arm and hand muscles. It can be observed that in both subjects stimulation of the C7 root induces specific responses in the tricep muscles, while stimulation of the C8 root induces muscle responses in the extrinsic hand muscles but not in the triceps.

We applied monopolar cathodic stimulation of the dorsal cervical roots with a counter electrode located in the subdermal region of the coccyx. Contrary to the lumbar region, dorsal roots of the cervical spinal cord enter the spinal cord at an angle comprised between 90 and 45 degrees (FIG. 5). This anatomical organization provides a robust and well separated topology. The cervical roots are physically separated along the cord, and this increases the specificity of stimulation. Active sites can be located over each of the cervical roots with a longitudinal configuration (FIG. 5).

We stimulated the C7 and C8 roots in both patients and showed that during stimulation of the C7 root, triceps muscles are mainly recruited, while during C8 stimulation, more distal muscles of the hand and forearm are instead selectively recruited. Latencies and shapes of evoked potentials suggest that these were mainly constituted by monosynaptic components, as in the case of lumbar EES.

Generalization to Other Spinal Cord Structures

We have demonstrated that tailoring of multi-electrode arrays for dorsal root stimulation can achieve high specificity both at the lumbar and cervical spinal cord. Similar conclusions can therefore be inferred for other regions in the cord. For instance, organization of the roots in the most sacral segments is similar to the cervical region; therefore, a longitudinal displacement of electrodes would reproduce the anatomical organization of the roots and allow for the results that we have shown in the lumbar and cervical spinal cord.

Time Specificity

Movement production is orchestrated by the coordinated activation of motorpools along the spinal cord that are activated with specific and precise timing by the central nervous system. After a spinal cord lesion, either cervical or thoracic, motorpools do not receive inputs from the supraspinal structures despite spinal motor circuits remaining functional. Therefore, effective therapies must aim at the precise activation of spinal circuits in space and time.

We have previously demonstrated how our multi-electrode arrays targeting dorsal roots and multipolar stimulation with independent sources and a common counter electrode can achieve high spatial specificity. In this section, we demonstrate how time specificity coupled to spatially selective implants can achieve superior performances than classic tonic stimulation protocols.

For this, we show an example application in the lumbar spinal cord of experimental rats.

Example 5

Software: Spatiotemporal Neuromodulation Adjusted Through Movement Feedback

Figure 7:
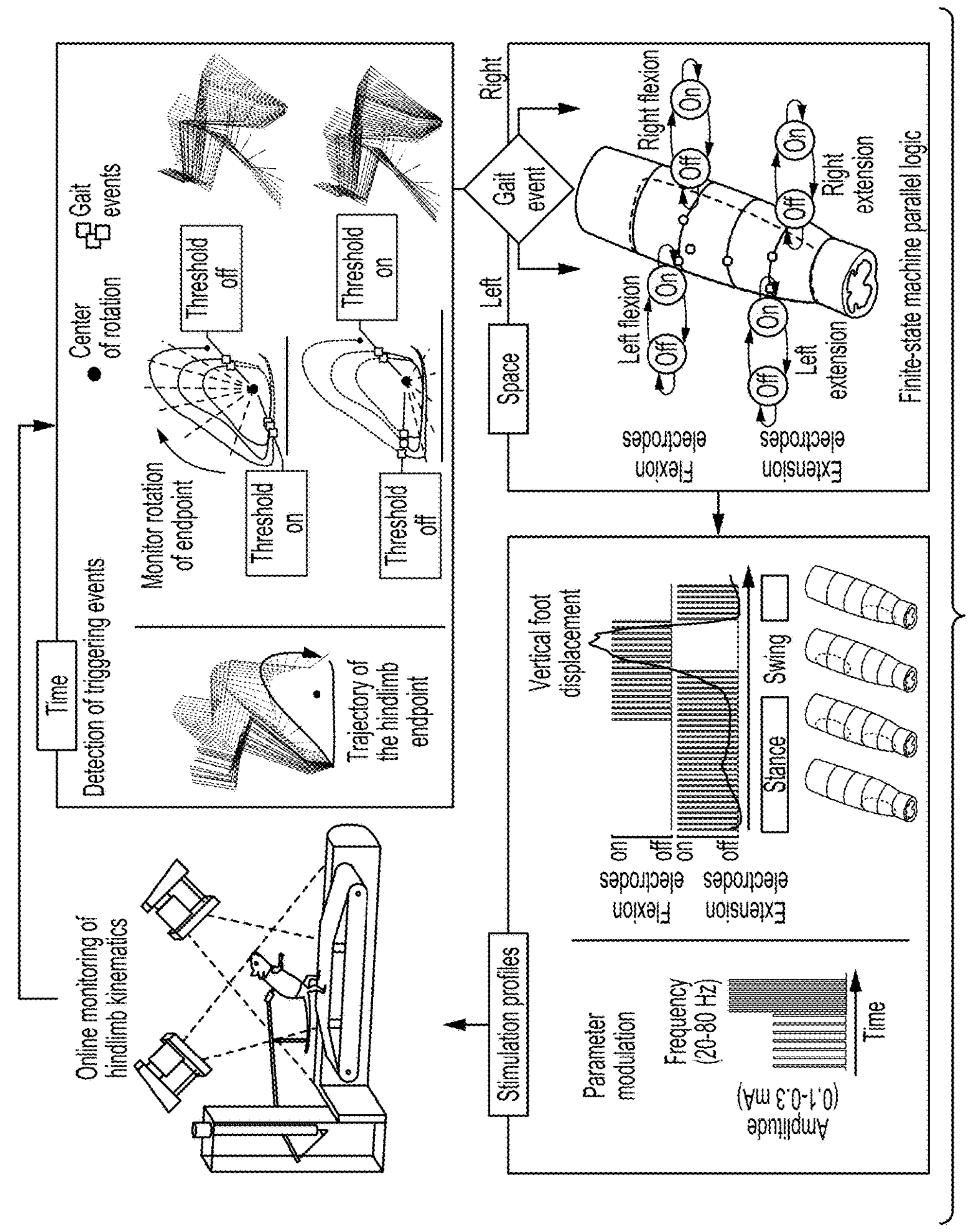
FIG. 7 shows a computational platform to trigger adjustments of the temporal structure, spatial configuration and stimulation parameters of the neuromodulation therapies. Rats were supported bipedally in a robotic system that provided vertical support during locomotion on a motorized treadmill belt. A high-resolution video system allowed real-time monitoring of the left and right limb endpoints (feet). The angular displacements of limb endpoints around a calculated center of rotation were converted into angular coordinates, as indicated with the dotted grey lines. The On and Off states of electrodes targeting extensor- and flexor-related hotspots were triggered when the angular coordinates crossed user-defined thresholds, personalized for each rat. The stimulation profile module enabled tuning the amplitude and frequency of stimulation based on the therapist or control policies. The diagram represents the relationship between the vertical displacement of the foot and the activation of extensor and flexor hotspot, and how the spatially selective electrodes were turned On and Off to replicate this activation pattern.

We exploited an advanced real-time control platform [7] to support the implementation of time specific stimulation patterns that, coupled to our spatially selective implants, we termed spatiotemporal neuromodulation therapies. We elaborated signal-processing algorithms that detected the timing of gait events based on real-time tracking of bilateral hindlimb kinematics (FIG. 7), as described above. For example, the continuous temporal sequence of gait events was derived from the angular displacements of the hindlimb endpoint (foot) around its continuously updated center of rotation (FIG. 7). This progression of the foot in space resembles a clock that divulges the current timing of gait.

A finite-state machine parallel logic (see Methods) triggered the activation of each electrode independently when the hindlimb endpoint trajectory crossed user-defined angular thresholds (FIG. 7). Additionally, adjustments in amplitude or frequency could be tuned using user-defined parameters or control policies [7] (FIG. 7). The time necessary to trigger stimulation based on movement feedback remained below 20 ms (see Methods). This processing time is 40 times faster than the average gait cycle duration in rats (800±146 ms). Stimulation was triggered with 97.8% accuracy for a temporal window constrained within less than 5% of the relative gait cycle duration (n=140 gait cycles).

This computational infrastructure provides the technological framework for a real-time adjustment of neuromodulation parameters over multiple electrodes based on high-fidelity kinematic feedback.

Example 6

Spatiotemporal Neuromodulation Reproduces Natural Hindlimb Motoneuron Activation We next exploited the developed hardware and software to develop temporally selective stimulation patterns and test whether spatiotemporal neuromodulation therapies ameliorated locomotion more than classical continuous stimulation protocols.

Figure 8:
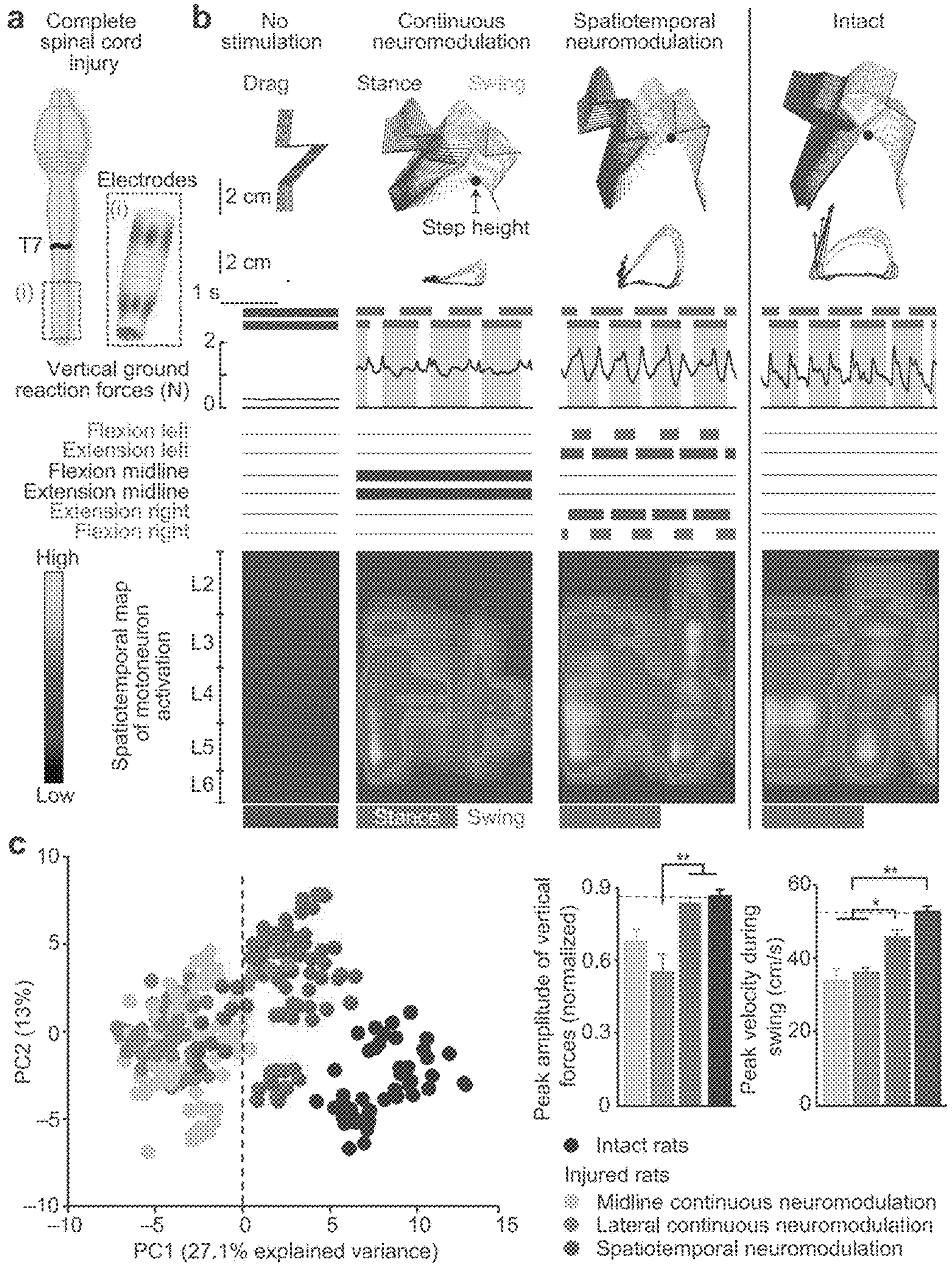
FIG. 8 shows (a) Rats receiving a complete SCI and a spinal implant with conventional midline electrodes and spatially selective lateral electrodes, as depicted in (i). (b) Locomotion was recorded on a treadmill without stimulation, with continuous neuromodulation applied over the midline of lumbar and sacral segments, and during spatiotemporal neuromodulation. For each condition (same rat) and an intact rat, a stick diagram decomposition of left limb movement is shown together with successive trajectories of the limb endpoint, the velocity and orientation of the foot trajectory at toe off (vector with arrowheads), the stance, drag and swing phases of both limbs, and vertical ground reaction forces during a continuous sequence of steps. The horizontal bars indicate the current state of the electrodes. The corresponding spatiotemporal maps of motoneuron activation were calculated over 10 consecutive steps. (c) All the gait cycles recorded in 5 rats under the different conditions of neuromodulation are represented in a PC space. Histogram plots report mean peak amplitude of vertical ground reaction forces and the mean peak velocity of the foot during swing for the different neuromodulation conditions and for intact rats. Error bars, SEM. *, $p<0.05$; **, $p<0.01$.

Adult rats received a complete spinal cord transection, and bipolar electrodes were inserted into hindlimb muscles and a spinal implant (FIG. 8*a*). Five weeks post-lesion, all rats exhibited complete hindlimb paralysis when positioned bipedally in a robotic bodyweight support system (e.g, support apparatus 140 of FIG. 11) [4] (FIG. 8*b*). Ten minutes prior to testing, we administered a serotoninergic replacement therapy [4, 5] that compensates for the interrupted source of monoaminergic modulation after injury. Continuous electrical neuromodulation delivered over the midline of L2/L3 and S1 segments enabled all of the tested rats to perform coordinated locomotion in response to treadmill motion, as previously reported [4] (FIG. 8*b*). However, the spatiotemporal map of motoneuron activation markedly differed from those observed in intact rats (FIG. 8*b*). The inappropriate spatiotemporal pattern of extensor and flexor motoneuron activation translated into reduced vertical ground reaction forces ($p<0.01$; FIG. 8*b*) and less extensive foot movement during swing ($p<0.01$; FIG. 8*b*) in injured compared to intact rats.

We next sought to optimize the temporal structure of spatiotemporal neuromodulation therapies. For this, we computed gait variables related to extension versus flexion components and evaluated the impact of varying the onset or end of stimulation through the spatially selective electrodes of a multi-electrode array. Adjustment of the activation timing for the electrode targeting the flexion components led to a gradual tuning of flexor muscle activity, step height, and foot acceleration during swing. The same modulation was detected for extensor muscle activity, vertical ground reaction force, and foot dragging when varying the activation timing of the electrode targeting the extension components. For each electrode, we selected a timing that yielded optimal values for this ensemble of gait parameters. The resulting temporal structure matched the temporal activation profiles of muscle synergies exposed in intact rats.

We tested whether this optimized stimulation protocol was capable of reproducing the spatiotemporal maps of motoneuron activation underlying locomotion of intact rats. In all tested rats, spatiotemporal neuromodulation therapies reinforced the amplitude of electromyographic signals and improved the activation timing in nearly all recorded hindlimb muscles. This robust modulation led to spatiotemporal maps of hindlimb motoneuron activation that resembled those observed in intact rats (FIG. 8*b*).

Finally, we evaluated whether spatiotemporal neuromodulation improved hindlimb motor control compared to continuous neuromodulation. To quantify gait performance, we computed numerous parameters from kinematic, kinetic, and muscle activity recordings (n=137). To weight their relative importance objectively, we subjected all the parameters from all recorded gait cycles to a principal component (PC) analysis [4, 5]. We visualized gait patterns in the new space created by PC1-2, where PC1 explained the highest amount of variance (27%) and reflected the degree of similarity to intact rats (FIG. 8*c*). Analysis of scores on PC1 revealed that spatiotemporal neuromodulation promoted gait patterns closer to those of intact rats compared to continuous neuromodulation ($p<0.05$). Parameters that highly correlated ($|value|>0.5$, factor loadings) with PC1 were extracted and regrouped into functional clusters corresponding to basic movement features. This analysis revealed that spatiotemporal neuromodulation normalized many key features of hindlimb movements (41/137 significantly improved parameters). Continuous stimulation delivered through the 4 spatially selective lateral electrodes failed to improve gait performance ($p<0.05$; FIG. 8*c*), confirming the synergy between spatial selectivity and temporal structure.

Example 7

Selective Adjustment of Extension Versus Flexion Movements

We previously showed that modulation of stimulation amplitude and frequency led to gradual adjustments of hindlimb movements [7]. We asked whether this modulation could be superimposed onto spatiotemporal neuromodulation therapies.

Figure 9:
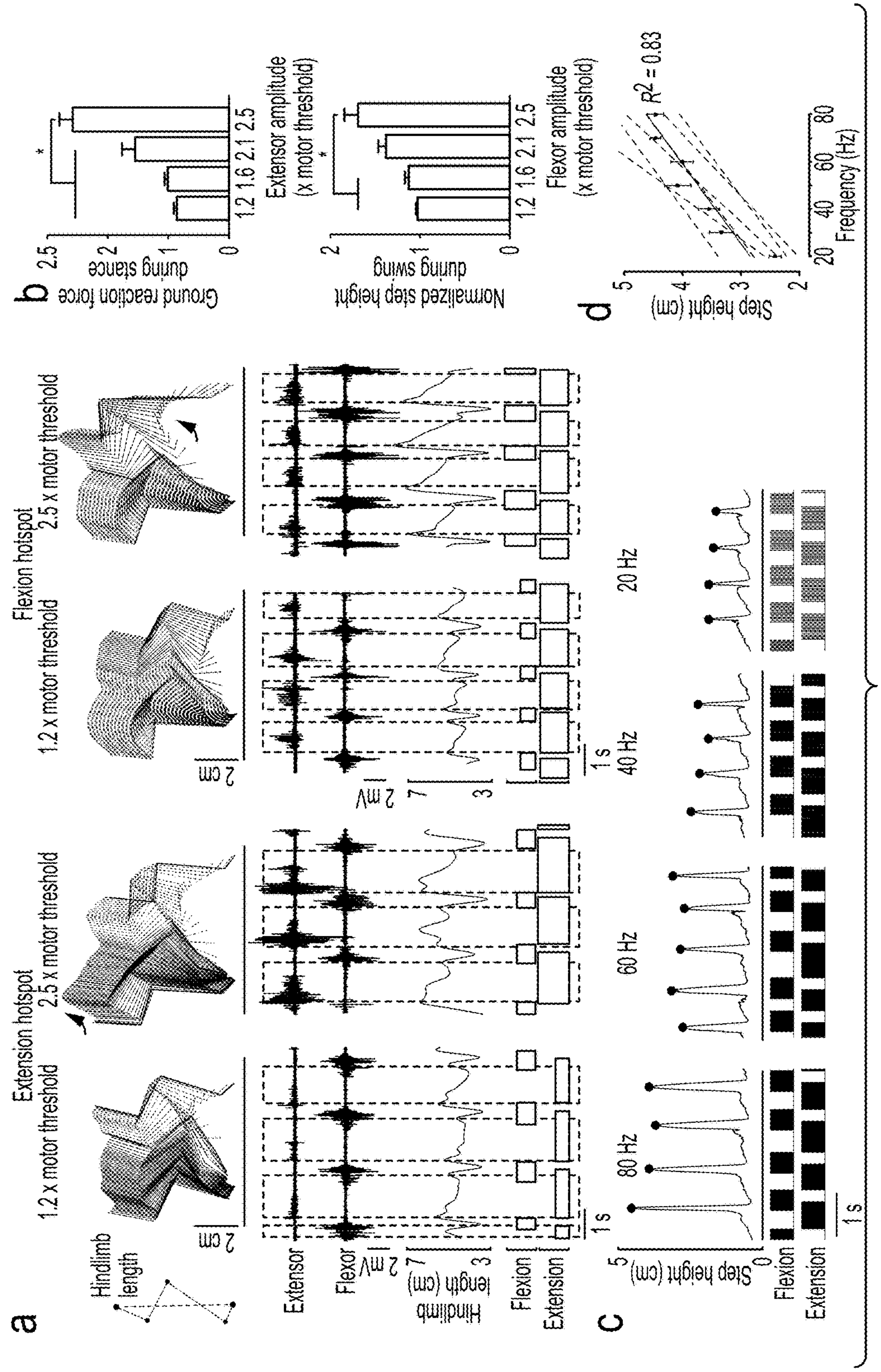
FIG. 9 shows (a) locomotor sequences recorded during spatiotemporal neuromodulation with two levels of stimulation amplitudes for the electrode targeting the extensor (left) versus flexor (right) hotspot. A representative stick diagram decomposition of limb movement is shown for each condition. The shadings correspond to the period during which the modulated electrode is turned on. Below, the electromyographic activity of extensor and flexor ankle muscles is displayed together with the changes in limb length for a series of steps. The upper right diagram explains the calculation of the limb length, which combines changes over multiple joints of the limb. The spatiotemporal pattern of stimulation is shown at the bottom. The height of the bars is proportional to the stimulation amplitude. (b) Histogram plots reporting the mean vertical ground reaction forces measured during stance while modulating the amplitude of the extension electrode, and the mean step height measured during swing while modulating the flexion electrode are shown. (c) Vertical foot displacements during locomotion under different stimulation frequencies adjusted over both extension and flexion electrodes are shown. The dots highlight the step height. Each pulse of stimulation is represented in the spatiotemporal patterns of stimulation shown at the bottom. The plot displays the relationships between the stimulation frequency and the step height for all the rats together, and each rat individually (thin line). The number of rats is indicated in each panel. Error bars, SEM. *, $p<0.05$.
Figure 10:
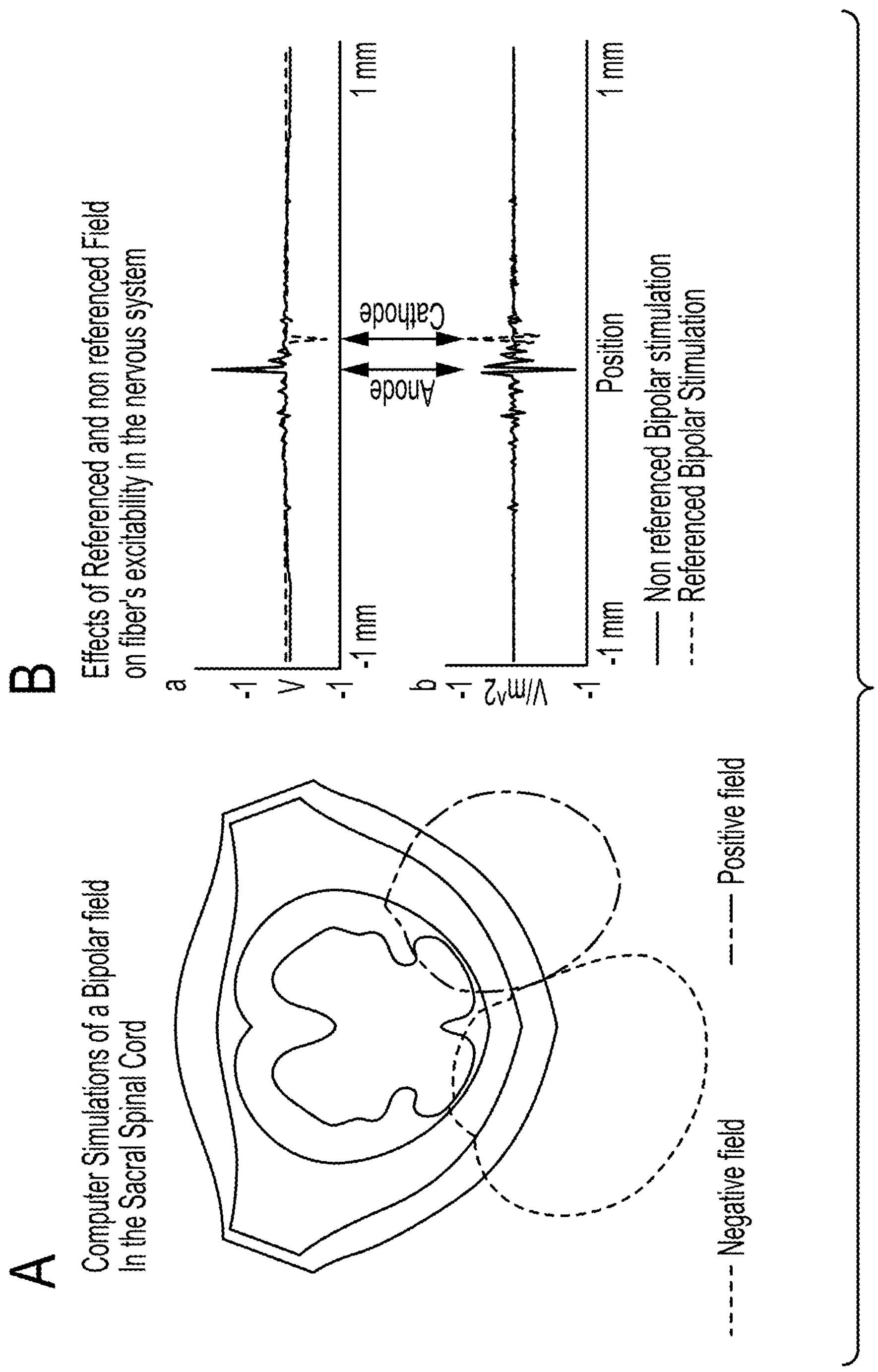
FIG. 10 shows A. simulations demonstrating that transversal bipolar EES can be used to modify the shape of the negative (excitatory) electric potential by introducing a positive field that "pushes" the negative field on the opposite direction. B. Simulations of the voltage field (a) and activation function (13) in the nervous system (b) for a classic bipolar stimulation and a referenced bipolar stimulation are shown.

We first varied the amplitude of stimulation delivered through one of the spatially selective lateral electrodes. A progressive increase of stimulation amplitude for the electrode targeting extension versus flexion promoted a selective and gradual augmentation of extensor versus flexor muscle activity on the stimulation side in all tested rats ($n=5$, $p<0.05$; FIG. 9*a*). This tuning translated into an incremental enhancement of extension versus flexion components (FIG. 9*b*), which supported the control of hindlimb extension during stance and foot trajectories during swing over ranges that reached the anatomical limits of motion. In contrast, an increase in stimulation amplitude rapidly blocked hindlimb movements when stimulation was delivered without temporal structure. Muscle activity resulted from a succession of motor responses elicited after each pulse of stimulation, which likely originated from the recruitment of proprioceptive feedback circuits [7, 12, 29, 30]. The increase in stimulation amplitude led to a commensurate augmentation of an amplitude of these motor responses.

We then verified that the previously observed modulation of step height with adjustment of stimulation frequency [7] was preserved during spatiotemporal neuromodulation. In all rats, adjustment of stimulation frequency led to a gradual and coordinated increase in both extension and flexion components. All rats exhibited a linear relationship between stimulation frequency and foot height (FIG. 9*c*). These relationships support control over complex foot trajectories during continuous locomotion [7] and can thus be combined with spatiotemporal neuromodulation.

REFERENCES

1. Borton, D., et al., *Personalized neuroprosthetics*. Sci Transl Med, 2013. 5(210): p. 210rv2.
2. Lozano, A. M. and N. Lipsman, *Probing and regulating dysfunctional circuits using deep brain stimulation*. Neuron, 2013. 77(3): p. 406-24.
3. Barthelemy, D., H. Leblond, and S. Rossignol, *Characteristics and mechanisms of locomotion induced by intraspinal microstimulation and dorsal root stimulation in spinal cats*. J Neurophysiol, 2007. 97(3): p. 1986-2000.
4. Courtine, G., et al., *Transformation of nonfunctional spinal circuits into functional states after the loss of brain input*. Nature neuroscience, 2009. 12(10): p. 1333-42.
5. van den Brand, R., et al., *Restoring voluntary control of locomotion after paralyzing spinal cord injury*. Science, 2012. 336(6085): p. 1182-5.
6. Holinski, B. J., et al., *Real-time control of walking using recordings from dorsal root ganglia*. J Neural Eng, 2013. 10(5): p. 056008.
7. Wenger, N., et al., *Closed-loop neuromodulation of spinal sensorimotor circuits controls refined locomotion after complete spinal cord injury*. Sci Transl Med, 2014. 6(255): p. 255ra133.
8. Carhart, M. R., et al., *Epidural spinal-cord stimulation facilitates recovery of functional walking following incomplete spinal-cord injury*. IEEE Trans Neural Syst Rehabil Eng, 2004. 12(1): p. 32-42.
9. Angeli, C. A., et al., *Altering spinal cord excitability enables voluntary movements after chronic complete paralysis in humans*. Brain, 2014.
10. Gerasimenko, Y., et al., *Noninvasive Reactivation of Motor Descending Control after Paralysis*. J Neurotrauma, 2015.
11. Herman, R., et al., *Spinal cord stimulation facilitates functional walking in a chronic, incomplete spinal cord injured*. Spinal Cord, 2002. 40(2): p. 65-8.
12. Capogrosso, M., et al., *A computational model for epidural electrical stimulation of spinal sensorimotor circuits*. J Neurosci, 2013. 33(49): p. 19326-40.
13. Rattay, F., K. Minassian, and M. R. Dimitrijevic, *Epidural electrical stimulation of posterior structures of the human lumbosacral cord: 2. quantitative analysis by computer modeling*. Spinal Cord, 2000. 38(8): p. 473-89.
14. Ladenbauer, J., et al., *Stimulation of the human lumbar spinal cord with implanted and surface electrodes: a computer simulation study*. IEEE Trans Neural Syst Rehabil Eng, 2010. 18(6): p. 637-45.
15. Hofstoetter, U.S., et al., *Periodic modulation of repetitively elicited monosynaptic reflexes of the human lumbosacral spinal cord*. J Neurophysiol, 2015: p. jn 00136 2015.
16. Gerasimenko, Y. P., et al., *Spinal cord reflexes induced by epidural spinal cord stimulation in normal awake rats*. J Neurosci Methods, 2006. 157(2): p. 253-63.
17. Sayenko, D. G., et al., *Neuromodulation of evoked muscle potentials induced by epidural spinal cord stimulation in paralyzed individuals*. J Neurophysiol, 2013.
18. Danner, S. M., et al., *Human spinal locomotor control is based on flexibly organized burst generators*. Brain, 2015. 138(Pt 3): p. 577-88.
19. Edgerton, V. R., et al., *Training locomotor networks*. Brain Res Rev, 2008. 57(1): p. 241-254.
20. Rejc, E., C. Angeli, and S. Harkema, *Effects of Lumbosacral Spinal Cord Epidural Stimulation for Standing after Chronic Complete Paralysis in Humans*. PLoS One, 2015. 10(7): p. e0133998.
21. Yakovenko, S., et al., *Spatiotemporal activation of lumbosacral motoneurons in the locomotor step cycle*. J Neurophysiol, 2002. 87(3): p. 1542-53.
22. Cappellini, G., et al., *Migration of motor pool activity in the spinal cord reflects body mechanics in human locomotion*. J Neurophysiol, 2010. 104(6): p. 3064-73.
23. Ivanenko, Y. P., et al., *Temporal components of the motor patterns expressed by the human spinal cord reflect foot kinematics*. J Neurophysiol, 2003. 90(5): p. 3555-65.
24. Dominici, N., et al., *Locomotor primitives in newborn babies and their development*. Science, 2011. 334(6058): p. 997-9.
25. Kiehn, O., *Locomotor circuits in the mammalian spinal cord*. Annu Rev Neurosci, 2006. 29: p. 279-306.
26. Zhang, T. C., J. J. Janik, and W. M. Grill, *Mechanisms and models of spinal cord stimulation for the treatment of neuropathic pain*. Brain Res, 2014. 1569: p. 19-31.
27. Minev, I. R., et al., *Electronic dura mater for long-term multimodal neural interfaces*. Science, 2015. 347(6218): p. 159-163.

28. Schirmer, C. M., et al., *Heuristic map of myotomal innervation in humans using direct intraoperative nerve root stimulation: Clinical article*. Journal of Neurosurgery: Spine, 2011. 15(1): p. 64-70.
29. Lavrov, I., et al., *Epidural stimulation induced modulation of spinal locomotor networks in adult spinal rats*. J Neurosci, 2008. 28(23): p. 6022-9.
30. Minassian, K., et al., *Stepping-like movements in humans with complete spinal cord injury induced by epidural stimulation of the lumbar cord: electromyographic study of compound muscle action potentials*. Spinal Cord, 2004. 42(7): p. 401-16.
31. van den Brand, R., et al., *Restoring Voluntary Control of Locomotion after Paralyzing Spinal Cord Injury*. Science, 2012. 336(6085): p. 1182-1185.
32. Dominici, N., et al., *Versatile robotic interface to evaluate, enable and train locomotion and balance after neuromotor disorders*. Nat Med, 2012. 18(7): p. 1142-7.
33. Gad, P. et al. *Development of a multi-electrode array for spinal cord epidural stimulation to facilitate stepping and standing after a complete spinal cord injury in adult rats*. Journal of neuroengineering and rehabilitation 10, 2 (2013).

The invention claimed is:

1. A system for spatiotemporal electrical neurostimulation of a spinal cord of a subject, comprising:

a signal processing device configured to receive signals from said subject and operate signal-processing algorithms to determine stimulation parameter settings;

one or more multi-electrode arrays configured to cover a portion of the spinal cord of said subject and apply selective spatiotemporal stimulation of spinal circuits and/or dorsal roots of the subject; and an Implantable Pulse Generator (IPG) configured to receive the stimulation parameter settings from said signal processing device and simultaneously deliver independent current or voltage pulses to the one or more multi-electrode arrays;

wherein said IPG is operatively connected with the signal processing device and the one or more multi-electrode arrays to provide a multipolar stimulation, where the multipolar stimulation directs a stimulation field to a desired anatomical location by modulating a shape of the stimulating field to enhance a spatial specificity of the electrical neuro stimulation; and wherein the system is configured and arranged to collect information about locomotor intention of the subject and decode this information by means of the signal processing device.

2. The system of claim 1, wherein said signals from the subject include one or more of neural signals, signals providing features of motion of said subject, kinematic signals, and electromyography signals.

3. The system of claim 1, wherein said IPG comprises a neutral returning electrode as reference.

4. The system of claim 1, wherein said signal processing device is included in said IPG.

5. The system of claim 1, wherein said one or more multi-electrode arrays is placed epidurally or subdurally in the spinal cord of said subject.

6. The system of claim 1, further comprising an apparatus for restoring control of neuromotor function to a subject suffering from a neuromotor impairment.

7. The system of claim 6, wherein said neuromotor impairment includes at least one of partial paralysis of limbs, total paralysis of limbs, immunological impairment, and loss of organ function.

8. The system of claim 6, wherein the apparatus comprises at least one of a treadmill, an exoskeleton, a robot-assisted body-weight support, and a multidirectional trunk support system.

9. The system of claim 6, wherein the apparatus is for use in a method for restoring voluntary control of locomotion in the subject suffering from the neuromotor impairment.

10. The system of claim 1, wherein the decoding is done by using machine-learning approaches.

11. The system of claim 1, wherein the system is a system for neuromotor impairment.

12. The system of claim 11, wherein the neuromotor impairment is a consequence of at least one of a spinal cord injury (SCI), an ischemic injury resulting from a stroke, or a neurodegenerative disease including Parkinson's disease.

13. A system for electrical neurostimulation of a spinal cord of a subject, comprising:

a pulse generator configured to simultaneously deliver independent current or voltage pulses to multiple electrodes; and one or more multi-electrode arrays configured to cover a portion of the spinal cord to selectively stimulate spinal circuits and/or dorsal roots, wherein said pulse generator is operatively connected with said one or more multi-electrode arrays to provide a multipolar stimulation that directs a stimulation field to a desired anatomical location by modulating a shape of the stimulating field to enhance a spatial specificity of the electrical neurostimulation; and wherein the system is configured and arranged to collect information about locomotor intention of the subject and decode this information by means of a signal processing device.

14. The system of claim 13, wherein the pulse generator is an Implanted Pulse Generator (IPG).

15. The system of claim 13, wherein a casing of said pulse generator is set as a neutral referencing ground.

16. The system of claim 13, wherein said one or more multi-electrode arrays is placed epidurally or subdurally in the spinal cord of said subject.

17. The system of claim 13, wherein said one or more multi-electrode arrays includes at least one portion comprising electrodes arranged in a transverse direction relative to the spinal cord and at least one portion comprising electrodes arranged in a longitudinal direction relative to the spinal cord.

18. The system of claim 13, wherein said one or more multi-electrode arrays comprises multiple electrodes arranged in two or more columns disposed in a longitudinal direction relative to the spinal cord.

19. The system of claim 13, wherein the decoding is done by using machine-learning approaches.

20. The system of claim 13, wherein the system is a system for neuromotor impairment.

21. The system of claim 20, wherein the neuromotor impairment is a consequence of at least one of a spinal cord injury (SCI), an ischemic injury resulting from a stroke, or a neurodegenerative disease, such as Parkinson's disease.

22. A closed-loop system for electrical neurostimulation of a spinal cord of a subject for a fine control of movement comprising:

a real-time monitoring component comprising sensors continuously acquiring feedback signals from said subject, operatively connected with a signal processing device configured to receive said feedback signals and operate real-time automatic control algorithms to determine electrical stimulation parameter settings, operatively connected with an Implantable Pulse Generator (IPG) configured to receive said stimulation parameter settings from said signal processing device and simultaneously deliver independent current or voltage pulses to multiple electrodes, operatively connected with one or more multi-electrode arrays configured to cover a portion of the spinal cord and apply a selective stimulation of spinal circuits and/or dorsal roots of the subject, wherein said IPG provides said one or more multi-electrode arrays with a multipolar stimulation that directs a stimulation field to a desired anatomical location by modulating a shape of the stimulating field to enhance a spatial specificity of the electrical neurostimulation; and wherein the closed-loop system is configured and arranged to collect information about locomotor intention of the subject and decode this information by means of the signal processing device.

23. The system of claim 22, wherein said one or more multi-electrode arrays includes at least one portion comprising electrodes arranged in a transverse direction relative to the spinal cord and at least one portion comprising electrodes arranged in a longitudinal direction relative to the spinal cord.

24. The system of claim 22, wherein said one or more multi-electrode arrays comprises multiple electrodes arranged in two or more columns disposed in a longitudinal direction relative to the spinal cord.

25. The system of claim 22, wherein the signal processing device is configured to execute a method for restoring voluntary control of locomotion in a subject suffering from a neuromotor impairment.

26. The system of claim 22, further comprising an apparatus for restoring voluntary control of locomotion to a subject suffering from a neuromotor impairment.

27. The system of claim 26, wherein the apparatus comprises at least one of a treadmill, an exoskeleton, a robot-assisted body-weight support, and a multidirectional trunk support system.

28. The system of claim 22, wherein the decoding is done by using machine-learning approaches.

29. The system of claim 22, wherein the system is a system for neuromotor impairment.

30. The system of claim 29, wherein the neuromotor impairment is a consequence of at least one of a spinal cord injury (SCI), an ischemic injury resulting from a stroke, or a neurodegenerative disease, such as Parkinson's disease.

* * * * *